United States Patent
Litvack et al.

(10) Patent No.: US 11,311,476 B2
(45) Date of Patent: *Apr. 26, 2022

(54) COMPOSITIONS AND USES OF ALPHA-ADRENERGIC AGENTS

(71) Applicant: Levation Pharma Ltd., Beverly Hills, CA (US)

(72) Inventors: Frank Litvack, Los Angeles, CA (US); Houman Hemmati, Los Angeles, CA (US)

(73) Assignee: Levation Pharma Ltd., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/061,869

(22) Filed: Oct. 2, 2020

(65) Prior Publication Data

US 2021/0259955 A1 Aug. 26, 2021

Related U.S. Application Data

(63) Continuation of application No. 16/043,725, filed on Jul. 24, 2018, now Pat. No. 10,828,252, which is a continuation of application No. PCT/US2017/015181, filed on Jan. 26, 2017.

(60) Provisional application No. 62/287,391, filed on Jan. 26, 2016.

(51) Int. Cl.
*A61K 9/00* (2006.01)
*A61K 31/4174* (2006.01)
*A61P 21/00* (2006.01)
*A61P 27/02* (2006.01)
*A61Q 19/00* (2006.01)
*A61K 8/49* (2006.01)
*A61Q 1/10* (2006.01)

(52) U.S. Cl.
CPC .......... *A61K 9/0014* (2013.01); *A61K 8/4946* (2013.01); *A61K 9/0019* (2013.01); *A61K 9/0048* (2013.01); *A61K 31/4174* (2013.01); *A61P 21/00* (2018.01); *A61P 27/02* (2018.01); *A61Q 1/10* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 8,357,714 B2 | 1/2013 | Silverberg | |
| 8,883,838 B2 | 11/2014 | Shanler et al. | |
| 9,801,857 B2 | 10/2017 | Sarpotdar et al. | |
| 10,828,252 B2 | 11/2020 | Litvack et al. | |
| 2007/0264318 A1 | 11/2007 | Chapin et al. | |
| 2009/0136598 A1 | 5/2009 | Chapin et al. | |
| 2011/0104206 A1 | 5/2011 | Nanduri et al. | |
| 2012/0058056 A1 | 3/2012 | Guo | |
| 2012/0225918 A1 | 9/2012 | Silverberg | |
| 2012/0225919 A1 | 9/2012 | Silverberg | |
| 2013/0035338 A1 | 2/2013 | Tang | |
| 2013/0079379 A1 | 3/2013 | Shanler et al. | |
| 2015/0150770 A1 | 6/2015 | Morariu | |
| 2016/0038465 A1 | 2/2016 | Silverberg et al. | |

FOREIGN PATENT DOCUMENTS

| | | |
|---|---|---|
| CN | 1738610 A | 2/2006 |
| CN | 101977595 A | 2/2011 |
| CN | 103501771 A | 1/2014 |
| EP | 1591110 A1 | 11/2005 |
| JP | 2011503061 A | 1/2011 |
| WO | WO-2009061431 A2 | 5/2009 |
| WO | WO-2011053792 A2 | 5/2011 |
| WO | WO-2017011271 A1 | 1/2017 |
| WO | WO-2017132410 A1 | 8/2017 |

OTHER PUBLICATIONS

Co-pending U.S. Appl. No. 17/064,327, inventors Litvack; Frank et al., filed Oct. 6, 2020.
EP17744911.3 The Extended European Search Report dated Jun. 18, 2019.
Niamtu, J. Botulinum toxin A: a review of 1,085 oral and maxillofacial patient treatments. J Oral Maxillofac Surg. Mar. 2003;61(3):317-24.
PCT/US2017/15181 International Search Report and Written Opinion dated Apr. 12, 2017.
Sajja, et al. Müller's Muscle Conjunctival Resection Ptosis Repair in the Aesthetic Patient. Saudi J Ophthalmol. Jan. 2011; 25(1): 51-60.
U.S. Appl. No. 16/043,725 Notice of Allowance dated Aug. 21, 2020.
U.S. Appl. No. 16/043,725 Office Action dated Aug. 9, 2019.
U.S. Appl. No. 16/043,725 Office Action dated Jan. 2, 2020.
U.S. Appl. No. 16/043,725 Office Action dated Mar. 5, 2019.
Yano, et al. Selective alpha 1A-adrenoceptor stimulation induces Mueller's smooth muscle contraction in an isolated canine upper eyelid preparation. Curr Eye Res. May 2010;35(5):363-9.

*Primary Examiner* — Robert A Wax
*Assistant Examiner* — Randeep Singh
(74) *Attorney, Agent, or Firm* — Wilson Sonsini Goodrich & Rosati

(57) ABSTRACT

The disclosure provides cosmetic and therapeutic compositions of alpha-adrenergic agents. Compositions of the disclosure may be used for topical, transdermal or parenteral administration to the eye or eyelid. The compositions of the disclosure may be used cosmetically to improve the appearance of the eye or therapeutically to treat ptosis.

19 Claims, No Drawings

COMPOSITIONS AND USES OF ALPHA-ADRENERGIC AGENTS

CROSS-REFERENCE

This application is a Continuation Application of U.S. application Ser. No. 16/043,725, filed Jul. 24, 2018, which is a Continuation Application of International Patent Application PCT/US2017/015181, filed Jan. 26, 2017, which claims the benefit of U.S. Provisional Application No. 62/287,391, filed Jan. 26, 2016, each of which is incorporated by reference herein in its entirety.

BACKGROUND OF THE INVENTION

Blepharoplasty is a surgical procedure that involves removal of excess skin, muscle, and fat from the eyelid of a subject. Blepharoplasty may be prescribed as a treatment for a droopy eyelid, referred to as ptosis, but may also be used to improve the line of vision or change the cosmetic appearance of the eyes of a subject. The procedure was one of the top five most commonly performed cosmetic procedures in the United States with over 200,000 surgeries performed in 2014, according to the 2014 Plastic Surgery Report of the American Society of Plastic Surgeons.

Blepharoplasty is an expensive procedure and not accessible to all individuals who need or want the surgery to repair ptosis or improve their eyesight or appearance. The average cost of blepharoplasy in the U.S. in 2014 was approximately $2900 as reported by the American Society of Plastic Surgeons. While the cost may be covered by health insurance carriers in particular circumstances, health insurers generally do not cover the cost of cosmetic surgery or its complications.

Non-surgical alternatives to blepharoplasy such as crutch glasses or special scleral contact lenses to support the eyelid may be used, however, these alternatives are cumbersome to wear and may not provide adequate relief for subjects. The available surgical alternatives are also inadequate for individuals seeking cosmetic improvements. Therefore there remains a need for non-surgical alternatives to blepharoplasty for therapeutic and cosmetic uses.

SUMMARY OF THE INVENTION

The disclosure provides an eyeshadow composition, comprising a dermatologically acceptable carrier, an agent that stimulates Müller's muscle, and at least one cosmetic excipient. In certain embodiments of the eyeshadow composition, the agent that stimulates Müller's muscle comprises an alpha-adrenergic agent. In certain embodiments of the eyeshadow composition, the alpha-adrenergic agent is selected from naturally occurring or synthetic alpha-adrenergic agents. In certain embodiments of the eyeshadow composition, the alpha-adrenergic agent is selected from an alpha-1 agonist and an alpha-2 agonist. In certain embodiments of the eyeshadow composition, the alpha-adrenergic agent is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluronorepinephrine, 6-fluoronorepinephrine, indanidine, levonordefrin, metaraminol, methoxamine, methyldopa, midodrine, naphazoline, norepinephrine (noradrenaline), octopamine, oxymetazoline, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a]imidazole, A-61603 (N-[5-(4,5-dihydro-1H-imidazol-2-yl)-2-hydroxy-5,6,7,8-tetrahydronaphthalen-1-yl]methanesulfonamide), salts of any one thereof, and any combination thereof.

In certain embodiments of the eyeshadow composition, the alpha-adrenergic agent is oxymetazoline or a salt thereof. In certain embodiments of the eyeshadow composition, the alpha-adrenergic agent is oxymetazoline. In certain embodiments of the eyeshadow composition, the alpha-adrenergic agent is not oxymetazoline.

In certain embodiments of the eyeshadow composition, the dermatologically acceptable carrier is selected from a lotion, an oil, a cream, a butter, a gel, an ointment, a spray, a milk, and a powder. In certain embodiments of the eyeshadow composition, the dermatologically acceptable carrier is a powder. In certain embodiments of the eyeshadow composition, the cosmetic excipient is selected from sunscreens, fragrances, pigments, and antioxidants.

In certain aspects, the disclosure provides a dermatological composition comprising a dermatologically acceptable carrier, an alpha-adrenergic agent, and at least one permeation enhancer. In certain embodiments of the dermatological composition, the permeation enhancer increases skin permeation of the alpha-adrenergic agent by about 2-fold or greater. In certain embodiments of the dermatological composition, the permeation enhancer increases skin permeation of the alpha-adrenergic agent by about 3-fold or greater. In certain embodiments of the dermatological composition, the permeation enhancer increases skin permeation of the alpha-adrenergic agent by about 0.5 mm or more. In certain embodiments of the dermatological composition, the permeation enhancer increases skin permeation of the alpha-adrenergic agent by about 1.0 mm or more. In certain embodiments of the dermatological composition, the alpha-adrenergic permeates through the skin and septal fat pad to contact Müller's muscle. In certain embodiments of the dermatological composition, the permeation enhancer is selected from alcohols, sulfoxides, azones, pyrrolidones, ureas, alkyl-N,N-disubstituted aminoacetals, propylene glycol, surfactants, terpenes, terpenoids, fatty acids, esters, cyclodextrins, and any combination thereof. In certain embodiments of the dermatological composition, the permeation enhancer is selected from ethanol, propylene glycol, dodecyl-N,N-dimethyl-aminoacetate, ethylacetate, azone, sodium dodecyl sulfate, d-limonene, oleic acid, 1,3-diphenyl-urea, N-methyl-2-pyrrolidone, beta-cyclodextrin, dimethylsulfoxide, and any combination thereof. In certain embodiments of the dermatological composition, the composition further comprises one or more cosmetic excipients.

In certain aspects, the disclosure provides a dermatological composition comprising an alpha-adrenergic agent, at least one dermatologically acceptable carrier, and at least one cosmetic excipient selected from sunscreens, fragrances, pigments, and antioxidants. In certain embodiments of the dermatological composition, the dermatologically acceptable carrier is selected from a lotion, an oil, a cream, a butter, a gel, an ointment, a spray, a milk, and a powder. In certain embodiments of the dermatological composition, the alpha-adrenergic agent is selected from naturally occurring or synthetic alpha-adrenergic agents. In certain embodiments of the dermatological composition, the alpha-adrenergic agent is selected from an alpha-1 agonist and an alpha-2 agonist. In certain embodiments of the dermatological composition, the alpha-adrenergic agent is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluronorepinephrine, 6-fluoronorepinephrine, indanidine, levonordefrin, metaraminol, methoxamine, methyldopa, midodrine, naphazoline, norepinephrine (noradrenaline), octopamine, oxymetazoline, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a]imidazole, A-61603 (N-[5-(4,5-dihydro-1H-imidazol-2-yl)-2-hydroxy-5,6,7,8-tetrahydronaphthalen-1-yl]methanesulfonamide), salts of any one thereof, and any combination thereof.

In certain embodiments of the dermatological composition, the alpha-adrenergic agent is oxymetazoline or a salt thereof. In certain embodiments of the dermatological composition, the alpha-adrenergic agent is oxymetazoline. In certain embodiments of the dermatological composition, the alpha-adrenergic agent is not oxymetazoline. In certain embodiments of the dermatological composition, the composition comprises from about 0.5 µg to about 4 mg of the alpha-adrenergic agent per dose. In certain embodiments of the dermatological composition, the composition comprises from about 0.5 µg to about 2 mg of the alpha-adrenergic agent per dose.

Also disclosed herein is a controlled-release dermatological composition, comprising an alpha-adrenergic agent and a delivery system which controls the release of the alpha-adrenergic agent. In certain embodiments of the controlled-release dermatological composition, the composition is selected from a sustained-release composition, a prolonged-release composition, a pulsatile-release composition, and a delayed-release composition. In certain embodiments of the controlled-release dermatological composition, the delivery system is selected from polymer-based systems, porous matrices, hydrogel release systems, and peptide-based systems. In certain embodiments of the controlled-release dermatological composition, the composition is a sustained-release composition. In certain embodiments of the controlled-release dermatological composition, the composition is formulated for administration to the exterior surface of the eyelid. In certain embodiments of the controlled-release dermatological composition, the composition comprises from about 0.2 µg to about 6 mg of an alpha-adrenergic agent per dose. In certain embodiments of the controlled-release dermatological composition, the composition comprises from about 0.5 µg to about 4 mg of an alpha-adrenergic agent per dose. In certain embodiments of the controlled-release dermatological composition, the composition comprises from about 0.5 µg to about 3 mg of an alpha-adrenergic agent per dose.

In certain embodiments of the controlled-release dermatological composition, the composition is formulated as a lotion, a cream, a butter, a gel, an ointment, a spray, a milk, or a powder. In certain embodiments of the controlled-release dermatological composition, the composition further comprises at least one dermatologically acceptable carrier. In certain embodiments of the controlled-release dermatological composition, the composition further comprises one or more cosmetic excipients selected from sunscreens, fragrances, pigments, and antioxidants.

In certain embodiments of the controlled-release dermatological composition, the alpha-adrenergic agent is selected from naturally occurring or synthetic alpha-adrenergic agents. In certain embodiments of the controlled-release dermatological composition, the alpha-adrenergic agent is selected from an alpha-1 agonist and an alpha-2 agonist. In certain embodiments of the controlled-release dermatological composition, the alpha-adrenergic agent is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluronorepinephrine, 6-fluoronorepinephrine, indanidine, levonordefrin, metaraminol, methoxamine, methyldopa, midodrine, naphazoline, norepinephrine (noradrenaline), octopamine, oxymetazoline, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a]imidazole, A-61603 (N-[5-(4,5-dihydro-1H-imidazol-2-yl)-2-hydroxy-5,6,7,8-tetrahydronaphthalen-1-yl]methanesulfonamide), salts of any one thereof, and any combination thereof. In certain embodiments of the controlled-release dermatological composition, the alpha-adrenergic agent is oxymetazoline or a salt thereof.

Also disclosed herein is a method for treating ptosis of an eye of a subject in need thereof, comprising administering a composition comprising an alpha-adrenergic agent to the exterior surface of the eyelid of said eye of the subject. In certain embodiments of the method for treating ptosis, the composition is administered once, twice, or three times per day. In certain embodiments of the method for treating ptosis, the composition is selected from any one of the eyeshadow, the dermatological, or the controlled-release dermatological compositions described herein. In certain embodiments of the method for treating ptosis, the composition is not administered to the eyeball.

Also disclosed herein is a method for cosmetic therapy of an eye of a subject, comprising administering a composition comprising an alpha-adrenergic agent to the exterior surface of the eyelid of said eye of the subject. In certain embodiments of the method for cosmetic therapy, the composition is administered once, twice, or three times per day. In certain embodiments of the method for cosmetic therapy, the composition is selected from any one of the eyeshadow, the dermatological, or the controlled-release dermatological compositions described herein. In certain embodiments of the method for cosmetic therapy, the composition is not administered to the eyeball.

Also disclosed herein is a method for increasing the vertical separation of the upper and lower eyelids of an eye of a subject, comprising administering a composition comprising an effective amount of an alpha-adrenergic agent to the exterior surface of the eyelid of said eye of the subject. In certain embodiments of the method for increasing the vertical separation of the upper and lower eyelids, the method increases the vertical separation of the upper and lower eyelids by about 10 percent or more relative to the separation of the upper and lower eyelids prior to said administration. In certain embodiments of the method for increasing the vertical separation of the upper and lower eyelids, the composition is selected from any one of the eyeshadow, the dermatological, or the controlled-release dermatological compositions described herein. In certain embodiments of the method for increasing the vertical separation of the upper and lower eyelids, the subject does not have ptosis. In certain embodiments of the method for increasing the vertical separation of the upper and lower eyelids, the composition is not administered to the eyeball.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

The disclosure provides compositions and uses of alpha-adrenergic agents. In certain embodiments, the compositions of the disclosure comprise an alpha-adrenergic agent and are suitable for topical, transdermal, or parenteral administration. In particular embodiments, the disclosure provides controlled-release compositions of alpha-adrenergic agents for topical, transdermal, or parenteral administration. In particular embodiments, the alpha-adrenergic agent is an alpha-adrenergic agonist such as oxymetazoline.

The compositions of the disclosure may be used as an alternative to blepharoplasty for treating ptosis of a subject. In certain embodiments, the compositions of the disclosure are used to increase the vertical separation of the upper and lower eyelid of a subject or improve the visual axis of a subject without the need for an invasive surgical procedure. In particular embodiments, the composition is administered to a subject who does not suffer from ptosis. Compositions of the disclosure may be used for cosmetic purposes, such as to improve the appearance of the eyes.

In certain embodiments, the disclosure provides compositions, e.g., cosmetic compositions, for topical administration to the exterior surface of the eyelid, or any portion thereof, wherein the composition comprises an agent that stimulates Müller's muscle. Agents that stimulate Müller's muscle are known in the art and include, for example, alpha-adrenergic agents.

Alpha-Adrenergic Agents

In certain embodiments, the disclosure provides alpha-adrenergic agents which are compounds that modulate alpha-adrenergic receptors. Alpha-adrenergic agents of the disclosure may be selected from naturally occurring or synthetic alpha-adrenergic agents. In particular embodiments, the disclosure provides alpha-adrenergic agents that agonize one or more of alpha-1 and alpha-2 adrenergic receptors. In certain embodiments, the alpha-adrenergic agent agonizes alpha-1 and alpha-2 adrenergic receptors. In particular embodiments, the alpha-adrenergic agent agonizes alpha-1 and alpha-2 adrenergic receptors and is selected from a compound other than oxymetazoline. In particular embodiments, the disclosure provides alpha-adrenergic agents that antagonize one or more of alpha-1 and alpha-2 adrenergic receptors.

In certain embodiments, the alpha-adrenergic agent agonizes alpha-1 adrenergic receptors. In certain embodiments, the alpha-adrenergic agent selectively agonizes alpha-1 adrenergic receptors. In certain embodiments, the alpha-adrenergic agent agonizes alpha-2 adrenergic receptors. In certain embodiments, the alpha-adrenergic agent partially agonizes alpha-1 or alpha-2 adrenergic receptors. In certain embodiments, the alpha-adrenergic agonist is oxymetazoline. In particular embodiments, the alpha-adrenergic agent selectively agonizes alpha-1 adrenergic receptors and partially agonizes alpha-2 adrenergic receptors and is selected from a compound other than oxymetazoline.

The term "agonist," or a compound that "agonizes", as used herein, generally refers to a compound that binds to a specific receptor and triggers a response in the cell. An agonist generally mimics the action of an endogenous ligand that binds to the same receptor.

The term "antagonist," as used herein, refers to a molecule such as a compound, which diminishes, inhibits, or prevents a cellular response to a receptor activated by an agonist. Antagonists can include, but are not limited to, competitive antagonists, non-competitive antagonists, uncompetitive antagonists, partial agonists and inverse agonists. Competitive antagonists can reversibly bind to receptors at the same binding site (active site) as the endogenous ligand or agonist, without necessarily activating the receptor. Non-competitive antagonists (also known as allosteric antagonists) can bind to a distinctly separate binding site from the agonist, exerting their action to that receptor via the other binding site. Non-competitive antagonists generally do not compete with agonists for binding. Binding of a non-competitive antagonist to the receptor may result in a decreased affinity of an agonist to that receptor. Alternatively, binding of a non-competitive antagonist to a receptor may prevent a conformational change in the receptor required for agonist-mediated receptor activation. Non-competitive antagonists may require receptor activation by an agonist before they can bind to a separate allosteric binding site.

A "partial agonist" or a compound that "partially agonizes" refers to compounds which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

A "full agonist" or a compound that "fully agonizes" an alpha-adrenergic receptor, refers to a compound that activates a receptor producing full efficacy at that receptor.

As used herein, the term "selectively" agonize, refers to the ability of a compound described herein to agonize a target receptor with greater affinity than non-target receptors. Methods for determining whether a compound selectively agonizes alpha-1 or alph-2 adrenergic receptors are well known (e.g., A. Megans et al. Eur. J. Pharm. V. 129, I. 1-2, p 57-64 (1996)).

In certain embodiments, alpha-adrenergic agonists are selected from long-acting alpha-adrenergic agents and short-acting alpha-adrenergic agonists. As used herein, a "long-acting alpha-adrenergic agonist" is an alpha adrenergic agonist with a systemic half-life in normal adult humans of greater than three hours. Long-acting alpha adrenergic agonists include, without limitation, oxymetazoline, methoxamine, naphazoline, tetrahydrozoline, xylometazoline, and apraclonidine (also known as Iopidine®). In certain embodiments, the long-acting alpha-adrenergic agonist is oxymetazoline, with a reported half-life of 5 to 6 hours. In one embodiment, the long-acting alpha-adrenergic agonist is a pharmaceutically acceptable salt of the long-acting alpha-adrenergic agonist. In certain embodiments, the long-acting alpha-adrenergic agonist is oxymetazoline or a pharmaceutically acceptable salt thereof, e.g., oxymetazoline hydrochloride.

As used herein, a "short-acting alpha-adrenergic agonist" is an alpha-adrenergic agonist with a systemic half-life in normal adult humans of less than or equal to three hours. Short-acting alpha-adrenergic agonists include, without limitation, phenylephrine and brimonidine. In one embodiment the short-acting alpha-adrenergic agonist is a pharmaceutically acceptable salt of the short-acting alpha-adrenergic agonist. In certain embodiments, the short-acting alpha-adrenergic agonist is phenylephrine or a pharmaceutically acceptable salt thereof, e.g., phenylephrine hydrochloride.

In certain embodiments, the alpha-adrenergic agonist selectively agonizes alpha-1A adrenergic receptors. In certain embodiments, the alpha-adrenergic agonist selectively agonizes alpha-1B adrenergic receptors. In certain embodiments, the alpha-adrenergic agonist selectively agonizes alpha-1D adrenergic receptors. In certain embodiments, the alpha-adrenergic agonist selectively agonizes alpha-2A adrenergic receptors. In certain embodiments, the alpha-adrenergic agonist selectively agonizes alpha-2B adrenergic receptors. In certain embodiments, the alpha-adrenergic agonist selectively agonizes alpha-2C adrenergic receptors.

In certain embodiments, the alpha-1 adrenergic agonist is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluoronorepinephrine, 6-fluoronorepinephrine, indanidine, levonordefrin, metaraminol, methoxamine, methyldopa, midodrine, naphazoline, norepinephrine (noradrenaline), octopamine, oxymetazoline, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a] imidazole, A-61603 (N-[5-(4,5-dihydro-1H-imidazol-2-yl)-2-hydroxy-5,6,7,8-tetrahydronaphthalen-1-yl]methanesulfonamide), a salt of any one thereof, and any combination thereof. In certain embodiments, the alpha-1 adrenergic agonist is oxymetazoline or a salt thereof.

In certain embodiments, the alpha-1 adrenergic agonist is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluoronorepinephrine, 6-fluoronorepinephrine, indanidine, levonordefrin, metaraminol, methoxamine, methyldopa, midodrine, naphazoline, norepinephrine (noradrenaline), octopamine, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a] imidazole, A-61603 (N-[5-(4,5-dihydro-1H-imidazol-2-yl)-2-hydroxy-5,6,7,8-tetrahydronaphthalen-1-yl] methanesulfonamide), a salt of any one thereof, and any combination thereof.

In certain embodiments, the alpha-adrenergic agonist is a selective alpha-1A adrenergic agonist. In some embodiments, the alpha-1A selective adrenergic agonist is 6-(5-fluoro-2-pyrimidin-5-yl-phenyl)-6,7-dihydro-5H-pyrrolo[1,2-a]imidazole or A-61603 (N-[5-(4,5-dihydro-1H-imidazol-2-yl)-2-hydroxy-5,6,7,8-tetrahydronaphthalen-1-yl] methanesulfonamide).

In certain embodiments, the alpha-adrenergic agent is an alpha-2 adrenergic agonist. In certain embodiments, the alpha-2 adrenergic agonist is selected from agmatine, amitraz, apraclonidine (lopidine), brimonidine, cannabigerol, cannabivarin, clonidine, detomidine, dexmedetomidine, dihydroergotamine, dipivefrine, dopamine, ephedrine, ergotamine, epinephrine (adrenaline), esproquin, etilefrin, ethylnorepinephrine, fadolmidine, 6-fluoronorepinephrine, guanabenz, guanfacine, guanoxabenz, levonordefrin, lofexidine, marsanidine, 7-Me-marsanidine, medetomidine, methamphetamine, methyldopa, mivazerol, naphazoline, 4-NEMD (4-(1-naphthalen-1-ylethyl)-1H-imidazole), (R)-3-nitrobiphenyline, norepinephrine (noradrenaline), phenylpropanolamine, piperoxan, pseudoephedrine, rilmenidine, romifidine, talipexole, tetrahydrozoline, tizanidine, tolonidine, urapidil, xylazine, xylometazoline, a salt of any one thereof, and any combination thereof.

The compositions described herein may include at least one alpha-adrenergic agent as an active ingredient in free-acid or free-base form, or in a pharmaceutically acceptable salt form. Included in the present disclosure are salts, particularly pharmaceutically acceptable salts, of the alpha-adrenergic agents herein. The alpha-adrenergic agents of the disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The alpha-adrenergic agents described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). Active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the alpha-adrenergic agents presented herein are also considered to be disclosed herein. In some situations, the alpha-adrenergic agents may exist as tautomers. All tautomers are included within the scope of the compounds presented herein.

In certain embodiments, the alpha-adrenergic agent may be a prodrug, e.g., wherein a hydroxyl in the parent compound is presented as an ester, a carbonate, or carboxylic acid present in the parent compound is presented as an ester. In certain such embodiments, the prodrug is metabolized to the active parent compound in vivo, e.g., the ester is hydrolyzed to the corresponding hydroxyl, or acid.

Cosmetic and Pharmaceutical Compositions

In certain embodiments, provided herein are cosmetic and therapeutic compositions comprising an agent that stimulates Müller's muscle, e.g., an alpha-adrenergic agonist or a cosmetically or pharmaceutically acceptable salt, polymorph, solvate, prodrug, N-oxide or isomer thereof, and an excipient. In some embodiments, the alpha-adrenergic agents are formulated into pharmaceutical or cosmetic compositions. Cosmetic or pharmaceutical compositions may be formulated in a conventional manner using one or more pharmaceutically acceptable inactive ingredients that facilitate processing of the active compounds into preparations that can be used pharmaceutically or cosmetically. Proper formulation is dependent upon the route of administration chosen. Exemplary compositions of the disclosure include those found in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In certain embodiments, provided herein are pharmaceutical compositions that include an alpha-adrenergic agent as described herein and at least one cosmetic or pharmaceutically acceptable excipient. In certain embodiments, the at least one cosmetic or pharmaceutically acceptable excipient is selected from carriers, buffering agents, binders, filling agents, suspending agents, disintegrating agents, dispersing agents, surfactants, lubricants, diluents, solubilizers, plasticizers, stabilizers, wetting agents, anti-foaming agents, antioxidants, preservatives, pigments, or a combination thereof. In certain embodiments, the at least one cosmetic or pharmaceutically acceptable excipient is a cosmetic excipient, such as those described herein.

In certain embodiments, compositions of the disclosure include two or more alpha-adrenergic agents such as two alpha-adrenergic agents.

The compositions described herein are administered to a subject by appropriate administration routes, including but not limited to, parenteral (e.g., intravenous, subcutaneous, intramuscular), topical, or transdermal administration routes. The compositions described herein include, but are not limited to, aqueous liquid dispersions, liquids, gels, slurries, suspensions, self-emulsifying dispersions, solid solutions, liposomal dispersions, aerosols, powders, immediate release formulations, controlled-release compositions, lyophilized formulations, delayed-release formulations, extended-release formulations, pulsatile-release formulations, multiparticulate formulations, and mixed immediate and controlled-release compositions.

Compositions including an alpha-adrenergic agent described herein may be manufactured in a conventional manner, such as, by way of example only, by means of conventional mixing, dissolving, granulating, dragee-making, levigating, emulsifying, encapsulating, entrapping, or compression processes.

As will be understood by those skilled in the art, the most appropriate method of administering an alpha-adrenergic agent to a subject is dependent on a number of factors. In various embodiments, the alpha-adrenergic agent is administered topically to the eye or to the eyelid. In some embodiments, the alpha-adrenergic agent is administered topically to the eyelid such as to the exterior surface of the eyelid. In certain embodiments, the alpha-adrenergic agent is formulated for cosmetic application to the eyelid and may include additional agents such as sunscreens, vitamins, moisturizers (e.g., hyaluronic acid), antioxidants, pigments, natural oils or butters, or essential fatty acids. In certain embodiments, an alpha-adrenergic agent is formulated as a lotion or cosmetic, e.g., eyeshadow or eyeliner, for topical administration to the exterior surface of the eyelid.

In some embodiments, the alpha-adrenergic agent is administered parenterally, such as injected into the eyelid. The alpha-adrenergic agent may be injected intravenously into the eyelid or the surrounding area, such as injected into the angular vein. The alpha-adrenergic agent may be administered subcutaneously, such as administered by subcutaneous injection into the eyelid. In some embodiments, the alpha-adrenergic agent is administered intramuscularly, such as though injection into Müller's muscle in the eyelid. In certain embodiments, the alpha-adrenergic agent is administered pre-septally, post-septally, or into the post-septal fat pad.

Parenteral Formulation

In some embodiments, an agent that stimulates Müller's muscle, e.g., an alpha-adrenergic agent, is administered parenterally, such as by injection. Parenteral administration may involve bolus injection or continuous infusion. Formulations for injection may be presented in unit dosage form, e.g., in ampoules or in multi-dose containers, with an added preservative. The pharmaceutical composition described herein may be in a form suitable for parenteral injection, such as a sterile suspension, solution, or emulsion in oily or aqueous vehicles, and may contain additional agents such as suspending, stabilizing, and/or dispersing agents.

Formulations for parenteral administration include aqueous solutions of the alpha-adrenergic agent in water-soluble form. Additionally, suspensions of the alpha-adrenergic agent may be prepared as appropriate oily injection suspensions. Suitable lipophilic solvents or vehicles include fatty oils such as sesame oil; synthetic fatty acid esters, such as ethyl oleate; triglycerides; or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use. In certain embodiments, systems for pharmaceutical compounds may be employed, such as, for example, liposomes and emulsions.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

Formulations suitable for subcutaneous injection may also contain additives such as preserving, wetting, emulsifying, and dispensing agents. Prevention of the growth of microorganisms can be ensured by various antibacterial and antifungal agents. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, an alpha-adrenergic agent may be formulated in aqueous solutions, preferably in physiologically compatible buffers such as Hank's solution, Ringer's solution, or physiological saline buffer.

In various embodiments, the injectable composition comprises from about 0.1 µg to about 4 mg of the alpha-adrenergic agent per dose. In certain embodiments, the injectable composition comprises from about 0.1 mg to about 10 mg of the alpha-adrenergic agent per dose. In some embodiments the composition comprises about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, 2.1 mg, about 2.2 mg, about 2.3 mg, about 2.4 mg, about 2.5 mg, about 2.6 mg, about 2.7 mg, about 2.8 mg, about 2.9 mg, about 3.0 mg, 3.1 mg, about 3.2 mg, about 3.3 mg, about 3.4 mg, about 3.5 mg, about 3.6 mg, about 3.7 mg, about 3.8 mg, about 3.9 mg, about 4.0 mg, 4.1 mg, about 4.2 mg, about 4.3 mg, about 4.4 mg, about 4.5 mg, about 4.6 mg, about 4.7 mg, about 4.8 mg, about 4.9 mg, about 5.0 mg, 5.1 mg, about 5.2 mg, about 5.3 mg, about 5.4 mg, about 5.5 mg, about 5.6 mg, about 5.7 mg, about 5.8 mg, about 5.9 mg, about 6.0 mg, 6.1 mg, about 6.2 mg, about 6.3 mg, about 6.4 mg, about 6.5 mg, about 6.6 mg, about 6.7 mg, about 6.8 mg, about 6.9 mg, about 7.0 mg, 7.1 mg, about 7.2 mg, about 7.3 mg, about 7.4 mg, about 7.5 mg, about 7.6 mg, about 7.7 mg, about 7.8 mg, about 7.9 mg, about 8.0 mg, 8.1 mg, about 8.2 mg, about 8.3 mg, about 8.4 mg, about 8.5 mg, about 8.6 mg, about 8.7 mg, about 8.8 mg, about 8.9 mg, about 9.0 mg, 9.1 mg, about 9.2 mg, about 9.3 mg, about 9.4 mg, about 9.5 mg, about 9.6 mg, about 9.7 mg, about 9.8 mg, about 9.9 mg, or about 10 mg of the alpha-adrenergic agent per dose. In certain embodiments, any two of the doses in this paragraph may be combined to form a range of dosages included within the disclosure, e.g., the injectable composition comprises from about 1.0 mg to about 9.0 mg of an alpha-adrenergic agent per dose.

In some embodiments, the injectable composition comprises from about 0.1 mg to about 1 mg of the alpha-adrenergic agent per dose. In some embodiments, the injectable composition comprises from about 0.5 mg to about 1 mg of the alpha-adrenergic agent per dose. In some embodiments, the injectable composition comprises from about 1 mg to about 3 mg of the alpha-adrenergic agent per dose. In some embodiments, the injectable composition comprises from about 3 mg to about 5 mg of the alpha-adrenergic agent per dose.

In some embodiments, the injectable composition comprises 0.5 mg or less, e.g., from about 0.05 mg to about 0.4 mg, of the alpha-adrenergic agent per dose. In some embodiments, the injectable composition comprises 1 mg or less, e.g., from about 0.05 mg to about 0.9 mg, of the alpha-adrenergic agent per dose. In some embodiments, the injectable composition comprises 2 mg or less, e.g., from about 0.05 mg to about 1.9 mg, of the alpha-adrenergic agent per dose. In some embodiments, the injectable composition comprises 4 mg or less, e.g., from about 0.05 mg to about 3.9 mg, of the alpha-adrenergic agent per dose. In some embodiments, the injectable composition comprises at least 0.5 mg of the alpha-adrenergic agent per dose. In some embodiments, the injectable composition comprises at least 1 mg of the alpha-adrenergic agent per dose. In some embodiments, the injectable composition comprises at least 2 mg of the alpha-adrenergic agent per dose. In some embodiments, the injectable composition comprises at least 4 mg of the alpha-adrenergic agent per dose.

In some embodiments, the injectable composition comprises from about 0.5 µg to about 1 mg of the alpha-adrenergic agent per dose, e.g., from about 0.5 µg to about 10 µg, from about 0.5 µg to about 0.1 mg, from about 0.5 µg to about 0.5 mg, from about 10 µg to about 0.1 mg, from about 10 µg to about 0.5 mg, from about 0.1 mg to about 0.5 mg, or from about 0.1 mg to about 1 mg.

In various embodiments, a dose of the injectable composition is injected daily, weekly, or monthly as needed. In some embodiments, a dose of the injectable composition is injected once a day, twice a day, or three times a day, as needed. In some embodiments, a dose of the injectable composition is injected every other day. In certain embodiments, a dose of the injectable composition is injected every three days, every four days, or every five days.

Topical/Transdermal Formulation

In some embodiments, the alpha-adrenergic agent is formulated into a topically administrable composition. In some embodiments, the topical formulation is administered to the external surface of the eyelid. In some embodiments, the alpha-adrenergic agent is formulated into a transdermal administrable composition. In some embodiments, the transdermal formulation is administered to the external surface of the eyelid.

Topical Formulation

In certain embodiments, the alpha-adrenergic agent is administered topically to a subject. In certain embodiments, topical compositions of the disclosure are dermatological compositions and are applied to the surface of the skin, e.g., exterior surface of the eyelid such as the upper eyelid. In some embodiments, the topical formulation comprises an alpha-adrenergic agent and one or more excipients. In some embodiments, the topical formulation comprises a dermatologically acceptable carrier such as a dermatologically acceptable carrier conventional in the cosmetic, pharmaceutical, or dermatological fields. In certain embodiments, compositions of the disclosure further comprise at least one excipient. As used herein, the term "dermatologically acceptable carrier" refers to vehicles, diluents, and carriers known in the art to be suitable for use in dermatological compositions. A dermatologically acceptable carrier can further include adjuvants, additives, and excipients that enhance the carrier's structure and function, including but not limited to buffers, preservatives, gelling agents, rheological modifiers and stabilizers, moisturizers, and humectants. Suitable components are those known in the art to be suitable for use in contact with the skin of humans without undue toxicity, irritation, or allergic response. Suitable materials may be selected from the "Inventory of ingredients employed in cosmetic products," provided in European Commission Decision 2006/257/EC of Feb. 9, 2006.

Dermatologically acceptable carriers may be in the form of aqueous, aqueous/alcoholic or oily solutions; powders; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. The dermatologically acceptable carrier may take the physical form of a liquid, lotion, cream, butter, gel, ointment, or powder. In certain embodiments, the dermatologically acceptable carrier is selected from a carrier acceptable for administration to the exterior surface of the eyelid.

Water-containing emulsions, in the form of lotions or creams may permit an effective amount of the composition to be applied to the area of skin in need of treatment, do not rapidly dry out, and maintain contact of the skin with the alpha-adrenergic agent for an extended period of time. By moisturizing and softening the stratum corneum, lotions and creams also improve the rate of penetration of the alpha-adrenergic agent into the epidermis. In some embodiments, the lotion and cream compositions according to the invention comprise water and an effective amount of an emulsifier.

In some embodiments, the compositions comprise a dermatologically acceptable oil. Suitable oils are well known in the cosmetic arts, and include but are not limited to grapeseed oil, olive oil, sweet almond oil, avocado oil, sesame oil, canola oil, jojoba oil, and the like, as well as mineral oil and synthetic oils such as dimethicone. In some embodiments, the compositions comprise a semisolid triglyceride, including but not limited to shea butter, cocoa butter, illipe butter, mango butter, avocado butter or the like. In certain embodiments, the compositions comprise silicone.

In some embodiments, the compositions comprise a stiffener, such as stearic acid or 12-hydroxystearic acid. The amount of the stiffener may be varied depending on whether a lotion or cream is desired, for example. In certain embodiments, the topical compositions comprise hyaluronic acid or a salt thereof.

In some embodiments, the compositions comprise an emulsifier in order to uniformly incorporate water into the ointment, such as one or more of emulsifying wax NF, glyceryl stearate, cetearyl alcohol, or sodium stearoyl lactylate. In some embodiments, the compositions comprise humectants, including but not limited to glycerin, sugar alcohols, or aloe vera gel.

In certain embodiments, the carrier may comprise a thickener. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient.

In certain embodiments the dermatologically acceptable carrier comprises a powder. Powders of the compositions may be selected from chalk, talc, kaolin, starch, mica, smectite clays, chemically modified magnesium aluminum silicate, organically modified montmorillonite clay, hydrated aluminum silicate, fumed silica, aluminum starch octenyl succinate and mixtures thereof.

The compositions of the invention may include additives and adjuvants which are conventional in the cosmetic, pharmaceutical or dermatological field, such as gelling agents, preservatives, antioxidants, solvents, fragrances, fillers, bactericides, odor absorbers, sunscreens, or pigments. The amounts of these various additives and adjuvants are those conventionally used in the field, and, for example, range from about 0.01% to about 90% of the total weight of the composition. In particular embodiments, a composition of the disclosure comprises one or more cosmetic excipients suitable for administration to the exterior surface of the eyelid.

In certain embodiments, the compositions of the disclosure comprise an agent that stimulates Müller's muscle and at least one cosmetic excipient. A "cosmetic excipient", as used herein, refers to an excipient which is used to enhance one or more cosmetic properties of a composition, e.g., dermatological composition, described herein. In certain embodiments, a cosmetic property is the appearance, the smell, the texture, the ease of application, etc., of the composition. In certain embodiments, the cosmetic property is the effect of the use of the composition such as improving the appearance or texture of the skin, reducing the appearance of wrinkles, protecting the skin from radiation, covering up marks or blemishes on the skin, or any combination thereof.

An "eyeshadow composition", as described herein, refers to a composition suitable for administration to the exterior surface of the eyelid. An eyeshadow composition is not intended to be limited to any particular type of composition or method of application and can include, for example, liquids, creams, powders, etc., that are suitable for application, e.g., using an applicator, a finger, or a brush, etc., to the exterior surface of an eyelid or any portion thereof. Eyeshadow compositions of the disclosure may include one or more cosmetic excipients.

In some embodiments, the compositions comprise an effective amount of one or more preservatives, including but not limited to potassium sorbate, citric acid, propylparaben, methylparaben, glycol, tocopherol, diazolidinyl urea, and imidazolidinyl urea. In some embodiments, the compositions include any of the oils and triglycerides above, and may further comprise a hydrocarbon base such as hard paraffin, soft paraffin, microcrystalline wax, or ceresin wax. In some embodiments, non-hydrocarbon bases such as wool fat or beeswax are also employed.

In some embodiments, the composition comprises a sunscreen. In certain embodiments, the sunscreen is selected from zinc oxide, titanium dioxide, octyl methoxycinnamate, octyl salicylate, avobenzone, menthyl anthranilate, cinoxate, ecamsule, octyl salicylate, octyl mehtoxycinnamate, sulisobenzone, oxybenzone, and combination thereof.

In certain embodiments, compositions of the disclosure comprise one or more of the following: mica, PTFE, zinc stearate, silica, isoeicosane, polyisobutene, lauroyl lysine, dimethicone, boron nitride, polyethylene, phenoxyethanol, Nylon-12, caprylic/capric triglyceride, sorbic acid, sodium dehydroacetate, magnesium stearate, talc, ethylhexyl palmitate, ethylene/acrylic acid copolymer, poloxamer, synthetic wax, tin oxide, kaolin, triethylhexanoin, hydrogenated lecithin, tocopheryl acetate, caprylyl glycol, hexylene glycol, calcium sodium borosilicate, ethylhexylglycerin, synthetic sapphire, calcium aluminum borosilicate, C13-16 isoparaffin, octadecene, stearyl dimethicone, titanium dioxide CI 77891, iron oxides CI 77491CI 77492CI 77499, ultramarines CI 77007, carmine CI 75470, manganese violet CI 77742, yellow 5 Lake CI 19140, ferric ferrocyanide CI 77510, bismuth oxychloride CI 77163, chromium hydroxide green CI 77289, chromium oxide greens CI 77288, zinc oxide, blue 1 Lake CI 42090, ferric ammonium ferrocyanide CI 77510, bronze powder, DC black No. 2 CI 77266, and red 40 Lake CI 16035.

In some embodiments, the alpha-adrenergic agent is formulated as an eyeshadow composition suitable for administration to the exterior surface of the eyelid, e.g., the upper eyelid. In some embodiments, the eyeshadow comprises a powder. Suitable powders generally comprise a dry particulate matter that have a particles size of about 0.02 to about 200, preferably about 0.5 to about 100 microns. In some embodiments, the particulate matter is colored. Suitable powders that may be used in eyeshadow compositions include, for example, bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, and mixtures thereof. In some embodiments, the powders are surface treated with lecithin, amino acids, mineral oil, silicone oil, or various other agents either alone or in combination, to coat the powder surface and render the particles hydrophobic in nature.

In some embodiments, powders of eyeshadow compositions described herein comprise organic or inorganic pigments. Organic pigments may be selected from aromatic compounds including azo, indigoid, triphenylmethane, anthraquinone, and xanthine dyes which are designated as D&C and FD&C blues, browns, greens, oranges, reds, yellows, etc. Organic pigments may be selected from insoluble metallic salts of certified color additives, referred to as the Lakes. Inorganic pigments include iron oxides, ultramarine and chromium or chromium hydroxide colors, and mixtures thereof. The percentage of pigments used in the powder component will depend upon the type of cosmetic being formulated and is usually ranging from about 5 to about 50% of the total cosmetic composition. In some embodiments, the pigment to powder weight ratio ranges from about 1:20 to about 20:1 or about 1:10 to about 1:2.

In some embodiments, the topical composition comprises from about 0.1 µg to about 5 mg of the alpha-adrenergic agent per dose. In some embodiments, the topical composition comprises from about 0.5 µg to about 4 mg of the alpha-adrenergic agent per dose. In some embodiments, the topical composition comprises from about 1 µg to about 3 mg of the alpha-adrenergic agent per dose. In some embodiments, the topical composition comprises from about 3 µg to about 5 mg of the alpha-adrenergic agent per dose.

In some embodiments, the topical composition comprises from about 0.5 µg to about 1 mg of the alpha-adrenergic agent per dose, e.g., from about 0.5 µg to about 10 µg, from about 0.5 µg to about 0.1 mg, from about 0.5 µg to about 0.5 mg, from about 10 µg to about 0.1 mg, from about 10 µg to about 0.5 mg, from about 0.1 mg to about 0.5 mg, or from about 0.1 mg to about 1 mg per dose.

In some embodiments, the topical composition comprises about 0.5 mg or less, e.g., from about 0.5 µg to about 0.4 mg, of the alpha-adrenergic agent per dose. In some embodiments, the topical composition comprises about 1 mg or less, e.g., from about 0.5 µg to about 0.9 mg, of the alpha-adrenergic agent per dose. In some embodiments, the topical/transdermal composition comprises about 2 mg or less, e.g., from about 0.5 µg to about 1.9 mg, of the alpha-adrenergic agent per dose. In some embodiments, the topical composition comprises about 4 mg or less, e.g., from about 0.5 µg to about 3.9 mg, of the alpha-adrenergic agent per dose.

In some embodiments, the topical composition comprises at least about 0.5 µg of the alpha-adrenergic agent per dose. In some embodiments, the topical composition comprises at least about 1 µg of the alpha-adrenergic agent per dose. In some embodiments, the topical composition comprises at least about 2 µg of the alpha-adrenergic agent per dose. In some embodiments, the topical composition comprises at least about 4 µg of the alpha-adrenergic agent per dose.

In various embodiments, a dose of the topical composition is applied to the exterior surface of the eyelid of the subject as needed. In some embodiments, a dose of the topical composition is applied once a day, twice a day, three times a day, four times a day, five times a day, six times a day, seven times a day, eight times a day, nine times a day, or ten times a day. A dose of the topical composition may be applied to an eyelid of a subject from one to ten times a day, such as from one to five times a day. In certain embodiments, a dose of the topical composition is applied once every two days, once every three days, once every four days, once every five days, once every six days, or even once every seven days.

In certain embodiments, the topical composition provides sustained-release of the alpha-adrenergic agent. In certain embodiments, the topical composition comprises a delivery system which controls the release of the alpha-adrenergic agent to the subject. In various embodiments, the release of the alpha-adrenergic agent is sustained over a period of 4 hours or more after application, 5 hours or more after application, 6 hours or more after application, 7 hours or more after application, 8 hours or more after application, 9 hours or more after application, 10 hours or more after application, 11 hours or more after application, 12 hours or more after application, 14 hours or more after application, 16 hours or more after application, 18 hours or more after application, 20 hours or more after application, 22 hours or more after application or even 24 hours or more after application.

Transdermal Formulations

In some embodiments, the alpha-adrenergic agent is administered via transdermal formulation. In certain embodiments a transdermal formulation of the disclosure is a topical formulation, as described in the preceding section, with one or more additional excipients which facilitate transport across the skin. Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein incorporate certain pharmaceutically acceptable excipients which are conventional in the art. Transdermal formulations of the disclosure may comprise one or more of the carriers, excipients, and additives discussed in the preceding section. In one embodiment, the transdermal formulations described herein comprise an alpha-adrenergic agent and a permeation enhancer. In addition, transdermal formulations can include additional components such as, but not limited to, aqueous adjuvant, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

The term "permeation enhancer" refers to a substance used to modify, generally to increase, the rate of permeation through skin or other body tissue of the alpha-adrenergic agent in the composition. Most known permeation enhancers fall into the following categories: alcohols (ethanol, pentanol, benzyl alcohol, lauryl alcohol, propylene glycols and glycerol), fatty acids (oleic acid, linoleic acid, valeric acid and lauric acid), amines (diethanolamine and triethanolamine), esters (isopropyl palmitate, isopropyl myristate and ethyl acetate), amides (1-dodecylazacycloheptane-2-one [Atone®], urea, dimethylacetamide, dimethylformamide and pyrrolidone derivatives), hydrocarbons (alkanes and squalene), surfactants (sodium laureate, cetyltrimethylammonium bromide, Brij®, Tween® and sodium cholate), terpenes (D-limonene, carvone and anise oil), sulfoxides (dimethyl sulfoxide) and phospholipids (lecithin). Other examples of permeation enhancer include amine oxides, unsaturated fatty acids, alpha-terpineol, and sorbitan monooleate. Amine oxides include, for example, lauramine oxide and 2-hexadecyldimethylamine oxide. Unsaturated fatty acids include, for example, oleic acid, linoleic acid, and linolenic acid. Sorbitan esters include, for example, sorbitan monooleate, sorbitan laurate, and sorbitan stearate. Isopropyl myristate and lauroglycol are also suitable for use as permeation enhancers. In some embodiments, a permeation enhancer of the compositions described herein, enhances permeation of an alpha-adrenergic agent into healthy skin, e.g., skin not effected by diseases or conditions such as rosacea, eczema, acne, psoriasis, etc. In general, healthy skin forms a formidable barrier to entry for pharmaceutical agents, such as alpha-adrenergic agents, whereas unhealthy skin is more permeable to such agents. Permeation enhancers that may enhance permeation of alpha-adrenergic agents into unhealthy skin may be insufficient to affect permeation of such agents, or permeation of such agents to the same depth, into healthy skin. In certain embodiments, a permeation enhancer of the compositions described herein may be characterized by significant permeation of an alpha-adrenergic agent into healthy skin, e.g., about 2-fold or more, about 3-fold or more, about 4-fold, or more about 5-fold or more, about 6-fold or more permeation relative to the permeation of such agent without a permeation enhancer. In certain embodiments, a permeation enhancer of the compositions described herein may permit permeation through the stratum corneum and septal fat pad to contact Müller's muscle. In certain embodiments, a permeation enhancer of the compositions described herein enables permeation of an alpha-adrenergic agent, e.g., oxymetazoline or a salt thereof, of up to about 3 mm, such as up to about 2.5 mm, such as up to about 2 mm deep into healthy skin.

In certain embodiments, the amount of permeation enhancer in the compositions of the disclosure is diminished relative to the amount used in compositions for unhealthy skin. For example, a composition of the disclosure may have up to about 10% less, up to about 20% less, up to about 30% less, up to about 40% less, up to about 50% less, up to about 60% less, up to about 70%, or even up to about 80% less than the amount of permeation enhancer needed to permeate the same agent to the same depth in unhealthy skin.

Examples of permeation enhancers are found in Pathan et al. ("Chemical Penetration Enhancers for Transdermal Drug Delivery Systems" Tropical Journal of Pharmaceutical Research, April 2009; 8 (2): 173-179); Som et al. ("Status of Surfactants as Penetration Enhancers in Transdermal Drug Delivery" J Pharm Bioallied Sci. 2012; 4(1): 2-9); and Trommer at al. ("Overcoming the Stratum Corneum: The Modulation of Skin Penetration" Skin Pharmacol Physiol 2006;19:106-121) all of which incorporated by reference in their entireties. In certain embodiments, the skin permeation is measured as shown in Franz T J "Percutaneous absorption. On the relevance of in vitro data" J. Invest. Dermatol 1975, 64:190-195, which is incorporated by reference in its entirety. In the experimental configuration for measuring skin permeation, a piece of skin (about 2.5 cm by 2.5 cm square) is mounted over a receptor well, fully filled with a solvent to ensure uniform contact with the underside of the skin piece. Clamped on top of the skin piece is a donor well into which the test formulation is introduced. Fluid samples can be abstracted from the receptor at given time intervals, and then analyzed for the concentration of the active. Retention of the active agent in the skin, or in the separate epidermal and dermal skin compartments, is then measured. Animal models utilizing pig skin are used to measure the permeation of active agents (See for example: Barbero et al. 2009 "Pig and guinea pig skin as surrogates for human in vitro penetration studies: a quantitative review" Toxicol. In Vitro 23, 1-13; Godin et al. 2007 "Transdermal skin delivery: predictions for humans from in vivo, ex vivo and animal models" Adv. Drug Deliv. Rev. 59, 1152-1161; Mahl et al. 2006 "The minipig in dermatotoxicology: methods and challenges" Exp. Toxicol. Pathol.57, 341-345; Yu et al. 2013 "Topical skin targeting effect of penetration modifiers on hairless mouse skin, pig abdominal skin and pig ear skin" Drug Delivery Vol. 22 , Iss. 8, 2015; and Simon et al. "The pig as an experimental animal model of per-cutaneous permeation in man: qualitative and quantitative observations - an overview" Skin Pharmacol. Appl. Skin Physiol. 200, 13, 229-234; all of which incorporated by reference in their entireties).

The permeation enhancer should be present in an amount sufficient to allow permeation of a sufficient amount of the alpha-adrenergic agent across the skin so as to have a desired therapeutic effect. The amount of permeation enhancer is typically less than about 40% by weight of the total composition, or less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, or less than about 10% by weight of the total composition.

In some embodiments, formulations suitable for transdermal administration of an alpha-adrenergic agent employ transdermal delivery devices and transdermal delivery patches. Such patches may be constructed for continuous, pulsatile, or on demand delivery of pharmaceutical agents. The rate of absorption can be slowed by using rate-controlling membranes or by trapping the compound within a polymer matrix or gel. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In some embodiments, the transdermal composition comprising an alpha-adrenergic agent is incorporated into different make-up products such as make-up foundation, fluid foundations and compact foundations, make-up removal lotions, make-up removal milks, eyeshadows, and powders.

In some embodiments, the transdermal composition comprises from about 0.1 µg to about 1 mg of the alpha-adrenergic agent per dose. In some embodiments, the transdermal composition comprises from about 0.5 µg to about 1 mg of the alpha-adrenergic agent per dose. In some embodiments, the transdermal composition comprises from about 1 µg to about 3 mg of the alpha-adrenergic agent per dose. In some embodiments, the transdermal composition comprises from about 3 µg to about 5 mg of the alpha-adrenergic agent per dose.

In some embodiments, the transdermal composition comprises from about 0.5 µg to about 1 mg of the alpha-adrenergic agent per dose, e.g., from about 0.5 µg to about 10 µg, from about 0.5 µg to about 0.1 mg, from about 0.5 µg to about 0.5 mg, from about 10 µg to about 0.1 mg, from about 10 µg to about 0.5 mg, from about 0.1 mg to about 0.5 mg, or from about 0.1 mg to about 1 mg.

In some embodiments, the transdermal composition comprises about 0.5 mg or less, e.g., from about 0.5 µg to about 0.4 mg, of the alpha-adrenergic agent per dose. In some embodiments, the transdermal composition comprises about 1 mg or less, e.g., from about 0.5 µg to about 0.9 mg, of the alpha-adrenergic agent per dose. In some embodiments, the topical/transdermal composition comprises about 2 mg or less, e.g., from about 0.5 µg to about 1.9 mg, of the alpha-adrenergic agent per dose. In some embodiments, the transdermal composition comprises about 4 mg or less, e.g., from about 0.5 µg to about 3.9 mg, of the alpha-adrenergic agent per dose.

In some embodiments, the transdermal composition comprises at least about 0.5 µg of the alpha-adrenergic agent per dose. In some embodiments, the transdermal composition comprises at least about 1 µg of the alpha-adrenergic agent per dose. In some embodiments, the transdermal composition comprises at least about 2 µg of the alpha-adrenergic agent per dose. In some embodiments, the topical/transdermal composition comprises at least about 4 µg of the alpha-adrenergic agent per dose.

In various embodiments, a dose of the transdermal composition is applied to the exterior surface of the eyelid of the subject as needed. In some embodiments, a dose of the transdermal composition is applied once a day, twice a day, three times a day, four times a day, five times a day, six times a day, seven times a day, eight times a day, nine times a day, or ten times a day. A dose of the topical/transdermal composition may be applied to an eyelid of a subject from one to ten times a day, such as from one to five times a day. In certain embodiments, a dose of the transdermal composition is applied once every two days, once every three days, once every four days, once every five days, once every six days, or even once every seven days.

In certain embodiments, the transdermal composition provides sustained-release of the alpha-adrenergic agent. In certain embodiments, the transdermal composition comprises a delivery system which controls the release of the alpha-adrenergic agent to the subject. In various embodiments, the release of the alpha-adrenergic agent is sustained over a period of 4 hours or more after application, 5 hours or more after application, 6 hours or more after application, 7 hours or more after application, 8 hours or more after application, 9 hours or more after application, 10 hours or more after application, 11 hours or more after application, 12 hours or more after application, 14 hours or more after application, 16 hours or more after application, 18 hours or more after application, 20 hours or more after application, 22 hours or more after application or even 24 hours or more after application.

Controlled-Release Compositions

In some embodiments, the alpha-adrenergic agent is administered to a subject as a controlled-release composition. In certain embodiments, a controlled-release composition comprises an alpha-adrenergic agent and a delivery system which controls the release of the alpha-adrenergic agent. In certain embodiments, the controlled-release composition comprises a delivery system and any of the alpha-adrenergic agent compositions described herein. In certain embodiments, a controlled-release composition comprises a topical or transdermal formulation, described in the preceding sections. Examples of delivery systems include, e.g., polymer-based systems such as implants or inserts; porous matrices; hydrogel release systems; transdermal patches; peptide-based systems; and contact lenses.

In some embodiments, the delivery system is a polymer-based implant. A polymer-based implant, such as a bioerodible implant, may be implanted into the eyelid or surrounding area and the polymer-based implant provides controlled-release of the alpha-adrenergic agent over a period of time. In some embodiments, the polymer-based implant is implanted surgically. In some embodiments, the implant is injected without the need for surgery. The polymer-based implant may be implanted subcutaneously or intramuscularly. In certain embodiments, the polymer-based implant may be implanted in close proximity to Müller's muscle, such as within about one millimeter, within about 2 millimeters, within about 3 millimeters, within about 4 millimeters or within about five millimeters of Müller's muscle.

In certain embodiments, the delivery system of the controlled-release composition comprises PLGA microparticles. PLGA is a biocompatible, biodegradable polymer which can be used to encapsulate compounds for sustained-release administration. In some embodiments, the lactic acid-glycolic acid copolymer is a PLGA-PEG-PLGA triblock copolymer. Methods for preparing PLGA microparticles and encapsulating compounds within the microparticles are well known in the art (e.g., M. H. Lee et al., Biomaterials Research (2009) 13(1):11-15).

In general, water soluble forms of an alpha-adrenergic agent will elute from a delivery system faster than less water soluble forms of the same drug. In certain embodiments, the disclosure provides compositions that allow for modulation of the rate of local delivery in vivo of an alpha-adrenergic agent from a delivery system. In particular, the rate of local delivery may be modulated by controlling the relative proportion of a more slowly eluting form of an alpha-adrenergic agent to a more rapidly eluting form of an alpha-adrenergic agent. Control of the water solubility of the agent to be delivered may be achieved in a number of ways such as by using a salt or non-salt form of an alpha-adrenergic agent. To control the release kinetics of alpha-adrenergic agent from a delivery system, two or more forms of an alpha-adrenergic agent with different solubilities may be combined in a proportion selected to achieve the desired kinetic profile.

To increase the water solubility of an alpha-adrenergic agent, the agent may be converted from a neutral or non-salt form to a salt form. The salt form of an alpha-adrenergic agent will likely be more water soluble than the non-salt or neutral form of the same alpha-adrenergic agent. Generally, the soluble salt form of the alpha-adrenergic agent will elute from the delivery system of the disclosure at a faster rate than a neutral form of the alpha-adrenergic agent. By controlling the relative proportions of the salt and non-salt forms of the alpha-adrenergic agent in the delivery systems of the disclosure, the rate and duration of drug delivery from the delivery system may be controlled.

In addition to the idea of controlling release through the combination of a salt and non-salt form of an alpha-adrenergic agent, the solubility of an alpha-adrenergic agent may also be modulated through the choice of a counterion for the salt form of the alpha-adrenergic agent. Counterions with greater hydrophilicity will generally increase elution rate while more hydrophobic counterions will reduce elution rate. For example, an alkali metal counterion would likely confer greater water solubility and faster elution rate than quaternary ammonium counter ions.

In certain embodiments, the delivery systems of the disclosure, such as polymer-based implants, have properties that help delay elution of the non-salt form of an alpha-adrenergic agent from the delivery system. Generally, the non-salt form of the alpha-adrenergic agent will have stronger intermolecular attraction to the polymer material of a delivery system and thereby slow the elution rate of the non-salt form of the alpha-adrenergic agent from the delivery system.

In certain embodiments, the controlled release composition of the disclosure comprises a delivery system, a first alpha-adrenergic agent in a free base or acid form and a second alpha-adrenergic agent in a salt form. In certain embodiments, the first alpha-adrenergic agent is an alpha-adrenergic agonist. In certain embodiments, the second alpha-adrenergic agent is an alpha-adrenergic agonist. In certain embodiments, the first alpha-adrenergic agent is the non-salt form, e.g., free base or acid, of the second alpha-adrenergic agent. For example, the first alpha-adrenergic agent is oxymetazoline and the second alpha-adrenergic agent is a salt of oxymetazoline. Alternatively, the second alpha-adrenergic agent may be a salt of a different alpha-adrenergic agent than the first alpha-adrenergic agent. For example, the first alpha-adrenergic agent may be oxymetazoline and the second alpha-adrenergic agent may be a salt of phenylephrine.

In certain embodiments, the compositions comprise a first alpha-adrenergic agent in a non-salt form and a second alpha adrenergic agent in a salt form in a weight ratio of about 95:5 to about 30:70, such as about 95:5 to about 50:50, such as about 95:5 to about 60:40.

Other ways to control elution rate of an alpha-adrenergic agent from a delivery system include, for example, using a biodegradable delivery system that releases the alpha-adrenergic agent as it degrades in vivo, using an inclusion complex in the composition, using a solubilizing agent in the composition, and selecting a crystalline or amorphous form of an alpha-adrenergic agent for the composition.

A. Polymer-Based Implants

In some embodiments, the polymer-based implant is solid polymeric implant. In certain embodiments, the polymer-based implant is a liquid or semi-solid that solidifies in-situ, e.g., upon injection into tissue, thereby forming the implant. Polymer-based implants may be implanted into the eyelid or surrounding area by surgical implantation or by injection.

In certain embodiments, the release of the alpha-adrenergic agent is sustained over a prescribed amount of time after implantation of the polymer-based implant. In various embodiments, the release of the alpha-adrenergic agent is sustained for up to one day, up to two days, up to three days, up to four days, up to five days, up to six days, up to seven days, up to one week, up to two weeks, up to three weeks, up to four weeks, up to one month, up to two months, up to three months, up to four months, up to five months, up to six months, up to seven months, up to eight months, up to nine months, up to ten months, up to eleven months, up to twelve months, or up to one year after implantation.

In various embodiments, the implant comprises from about 0.1 mg to about 10 mg of the alpha-adrenergic agent. In some embodiments, the implant comprises about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, 2.1 mg, about 2.2 mg, about 2.3 mg, about 2.4 mg, about 2.5 mg, about 2.6 mg, about 2.7 mg, about 2.8 mg, about 2.9 mg, about 3.0 mg, 3.1 mg, about 3.2 mg, about 3.3 mg, about 3.4 mg, about 3.5 mg, about 3.6 mg, about 3.7 mg, about 3.8 mg, about 3.9 mg, about 4.0 mg, 4.1 mg, about 4.2 mg, about 4.3 mg, about 4.4 mg, about 4.5 mg, about 4.6 mg, about 4.7 mg, about 4.8 mg, about 4.9 mg, about 5.0 mg, 5.1 mg, about 5.2 mg, about 5.3 mg, about 5.4 mg, about 5.5 mg, about 5.6 mg, about 5.7 mg, about 5.8 mg, about 5.9 mg, about 6.0 mg, 6.1 mg, about 6.2 mg, about 6.3 mg, about 6.4 mg, about 6.5 mg, about 6.6 mg, about 6.7 mg, about 6.8 mg, about 6.9 mg, about 7.0 mg, 7.1 mg, about 7.2 mg, about 7.3 mg, about 7.4 mg, about 7.5 mg, about 7.6 mg, about 7.7 mg, about 7.8 mg, about 7.9 mg, about 8.0 mg, 8.1 mg, about 8.2 mg, about 8.3 mg, about 8.4 mg, about 8.5 mg, about 8.6 mg, about 8.7 mg, about 8.8 mg, about 8.9 mg, about 9.0 mg, 9.1 mg, about 9.2 mg, about 9.3 mg, about 9.4 mg, about 9.5 mg, about 9.6 mg, about 9.7 mg, about 9.8 mg, about 9.9 mg, about 10 mg of the alpha-adrenergic agent. In certain embodiments, any two of the doses in this paragraph may be combined to form a range of dosages included within the disclosure, e.g., the implant comprises from about 1.0 mg to about 8.0 mg of an alpha-adrenergic agent.

In some embodiments, the implant comprises from about 0.1 mg to about 10 mg of the alpha-adrenergic agent. In some embodiments, the implant comprises from about 0.5 mg to about 8 mg of the alpha-adrenergic agent. In some embodiments, the implant comprises from about 2 mg to about 5 mg of the alpha-adrenergic agent. In some embodiments, the implant comprises from about 3 mg to about 5 mg of the alpha-adrenergic agent.

In some embodiments, the implant comprises about 10 mg or less of the alpha-adrenergic agent. In some embodiments, the implant comprises about 8 mg or less of the alpha-adrenergic agent. In some embodiments, the implant comprises about 6 mg or less of the alpha-adrenergic agent. In some embodiments, the implant comprises about 4 mg or less of the alpha-adrenergic agent.

In some embodiments, the implant comprises at least about 1 mg of the alpha-adrenergic agent. In some embodiments, the implant comprises at least about 2 mg of the alpha-adrenergic agent. In some embodiments, the implant comprises at least about 3 mg of the alpha-adrenergic agent. In some embodiments, the implant comprises at least about 4 mg of the alpha-adrenergic agent.

1. Solid Polymeric Implants

In certain embodiments, a solid polymer-based implant is used to administer the alpha-adrenergic agent. In some embodiments, the solid polymer-based implant in surgically implanted into the eyelid, such as implanted into the eyelid in close proximity to Müller's muscle. In some embodiments, the polymer-based implant comprises an alpha-adrenergic agent.

In various embodiments, the polymer of the polymer-based implant is selected from any polymer suitable for implantation into an animal. In certain embodiments, the polymer-based implant comprises a biodegradable polymer. "Biodegradable" is used to refer to any substance or object that can be decomposed by bacteria or another living organism. In some embodiments, the polymer is a biocompatible polymer. The terms "biocompatible polymer" and "biocompatibility" when used in relation to polymers are art-recognized. For example, biocompatible polymers include polymers that are neither themselves toxic to the host (e.g., a cell, an animal, or a human), nor degrade (if the polymer degrades) at a rate that produces monomeric or oligomeric subunits or other byproducts at toxic concentrations in the host.

In certain embodiments, toxicology of a biodegradable polymer intended for intracellular or in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible. Exemplary polymers that may be used in the polymer-based implants include: poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide)

(PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, silicones, polyalkylenes such as polyethylene, polypropylene, and polytetrafluoroethylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, poly(propylene fumarate), polyoxymethylene, poloxamers, poly(ortho)esters, poly(butyric acid), poly(valeric acid), poly(lactide-co-caprolactone), trimethylene carbonate, polyvinylpyrrolidone, polyalkyl cyanoacrylate, polyethylenimine, dioleyltrimethyammoniumpropane/dioleyl-sn-glycerolphosphoethanolamine, poly sebacic anhydrides, polyurethane, nylons, or copolymers thereof, and the polymers described in Shieh et al., 1994, J. Biomed. Mater. Res., 28, 1465-1475, and in U.S. Pat. No. 4,757,128, Hubbell et al., U.S. Pat. Nos. 5,654,381; 5,627,233; 5,628,863; 5,567,440; and 5,567,435. Other suitable polymers include polyorthoesters (e.g. as disclosed in Heller et al., 2000, Eur. J. Pharm. Biopharm., 50:121-128), polyphosphazenes (e.g. as disclosed in Vandorpe et al., 1997, Biomaterials, 18:1147-1152), and polyphosphoesters (e.g. as disclosed in Encyclopedia of Controlled Drug Delivery, pp. 45-60, Ed. E. Mathiowitz, John Wiley & Sons, Inc. New York, 1999), as well as blends and/or block copolymers of two or more such polymers. The carboxyl termini of lactide- and glycolide-containing polymers may optionally be capped, e.g., by esterification, and the hydroxyl termini may optionally be capped, e.g., by etherification or esterification. In certain embodiments, the polymer comprises or consists essentially of polyvinyl chloride (PVC), polymethyl methacrylate (PMMA) and decyl methacrylate or copolymers or any combination thereof. In polymers including lactic acid monomers, the lactic acid may be D-, L-, or any mixture of D- and L-isomers.

The polymer of the polymer-based implant may comprise a plasticizer, such as dioctyl sebacate (DOS), o-nitrophenyl-octylether, dimethyl phthalate, dioctylphenyl-phosphonate, dibutyl phthalate, hexamethylphosphoramide, dibutyl adipate, dioctyl phthalate, diundecyl phthalate, dioctyl adipate, dioctyl sebacate, or other suitable plasticizers. In certain embodiments, the plasticizer is poly(glycerol sebacate) (PGS). In certain embodiments, the plasticizer includes those disclosed in U.S. Pat. Nos. 2,784,127 and 4,444,933.

2. Injectable Polymeric Implants

Injectable polymeric implants of the disclosure refer to a liquid polymeric delivery system that can be injected into the eyelid where it forms a solid or semi-solid implant that releases the alpha-adrenergic agent in a controlled manner. In certain embodiments, the solid or semi-solid implant formed from the liquid polymeric delivery system is biodegradable. In certain embodiments, the liquid polymeric system is selected from thermoplastic polymers dissolved in a biocompatible solvent and thermosetting polymers that are liquids without the use of solvents. Thermosetting and thermoplastic formulations incorporate the advantages of an implant while circumventing the need for surgery for implantation of the implant.

a. Thermoplastic System

In certain embodiments, the liquid polymeric delivery system is a thermoplastic system. A thermoplastic system may be obtained when a solid, linear-chain, polymer is dissolved in a biocompatible solvent to form a liquid, which can then be combined with the alpha-adrenergic agent and administered via a syringe. In certain embodiments, the thermoplastic system is prepared from a formulation with one or more polymers. In certain embodiments, the polymer comprises a biodegradable polymer. Examples of biodegradable polymers which can be used in this application are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials. In some embodiments, the polymers have a lower degree of crystallization and are more hydrophobic. These polymers and copolymers may be more soluble in the biocompatible solvents than the highly crystalline polymers such as polyglycolide and chitin which also have a high degree of hydrogen-bonding. In some embodiments, the polymer is a polyactide, apolycaprolactone, and copolymers of these with glycolide in which there are more amorphous regions to enhance solubility.

In some embodiments, the solvent for the polymer is non-toxic, water miscible, and otherwise biocompatible. The solvents must also be biocompatible so that they do not cause severe tissue irritation or necrosis at the site of implantation. Furthermore, the solvent should be water miscible so that it will diffuse quickly into the body fluids and allow water to permeate into the polymer solution and cause it to coagulate or solidify. Examples of such solvents include, but are not limited to, N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one. In some embodiments, the solvent is N-methyl-2-pyrrolidone, 2-pyrrolidone, dimethyl sulfoxide, or acetone because of their solvating ability and their compatibility.

The solubility of the polymers in the various solvents will differ depending upon their crystallinity, their hydrophilicity, hydrogen-bonding, and molecular weight. Thus, not all of the polymers will be soluble in the same solvent, but each polymer or copolymer should have its optimum solvent. Lower molecular-weight polymers may dissolve more readily in the solvents than high-molecular-weight polymers. As a result, the concentration of a polymer dissolved in the various solvents will differ depending upon type of polymer and its molecular weight. Conversely, the higher molecular-weight polymers may tend to coagulate or solidify faster than the very low-molecular-weight polymers. Moreover the higher molecular-weight polymers will tend to give higher solution viscosities than the low-molecular-weight materials. Thus for optimum injection efficiency, the molecular weight and the concentration of the polymer in the solvent should be controlled.

For example, low-molecular-weight polylactic acid formed by the condensation of lactic acid will dissolve in N-methyl-2-pyrrolidone (NMP) to give a 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in NMP at only 50% by weight. The higher molecular-weight polymer solution coagulates immediately when placed into water. The low-molecular-weight polymer solution, although more concentrated, tends to coagulate very slowly when placed into water.

For polymers that tend to coagulate slowly, a solvent mixture can be used to increase the coagulation rate. For example, one liquid component of the mixture may be a good solvent for the polymer, and the other component is a poorer solvent or a non-solvent. The two liquids may be mixed at a ratio such that the polymer is still soluble but precipitates with the slightest increase in the amount of non-solvent, such as water in a physiological environment. By necessity, the solvent system must be miscible with both the polymer and water. An example of such a binary solvent system is the use of NMP and ethanol for low-molecular-weight DL-PLA. The addition of ethanol to the NMP/polymer solution increases its coagulation rate significantly.

It has also been found that solutions containing very high concentrations of high-molecular-weight polymers sometimes coagulate or solidify slower than more dilute solutions. It is suspected that the high concentration of polymer impedes the diffusion of solvent from within the polymer matrix and consequently prevents the permeation of water into the matrix where it can precipitate the polymer chains.

In some embodiments, the polymer comprises a block copolymer. In some embodiments, the block copolymer comprises hydrophilic poly(ethylene oxide) blocks and a hydrophobic poly(propylene oxide) blocks. In some embodiments, the block copolymer is a triblock of poly(ethylene oxide)-poly(propylene oxide)-poly(ethylene oxide) (marketed under the Pluronic™ or Poloxamer™ tradenames). In some embodiments, this triblock copolymer is dissolved in an aqueous solution. In some embodiments, the triblock copolymer absorbs water to form a gel. In some embodiments, the block copolymers are surface-active block copolymers which exhibit reverse thermal gelation behavior and possess drug-release characteristics.

The Pluronic™, Poloxamer™ type triblock copolymers undergo solidification or gelation as the temperature of the solution is raised above a critical temperature (gelation temperature). These polymers form micelles (microscopic spheres incorporating water) at low concentration and turn into thick, continuous gels at high concentrations and elevated temperature (~30° C.).

In some embodiments, the polymer comprises a lactic acid-glycolic acid copolymer. In some embodiments, the lactic acid-glycolic acid copolymer is a PLGA-PEG-PLGA triblock copolymer. Suitable PLGA-PEG-PLGA triblock copolymers are commercially available from PolySciTech (a Division of Akina, Inc.) of West Lafayette, Ind. Thermo-sensitive PLGA-PEG-PLGA triblock copolymers are well described in the art. These polymers may have molecular weights from about 2000 Da to about 40,000 Da, but may have any molecular weight provided that it has the required reverse thermo-sensitive properties. In some embodiments, the PLGA-PEG-PLGA triblock polymers may have a molecular weight of about 30,000 Da. In some other embodiments, the PLGA-PEG-PLGA triblock polymers may have a molecular weight of about 4000 Da. In some other embodiments, the PLGA-PEG-PLGA triblock copolymer may have a molecular weight distribution of 1500:1000:1500 but as one of ordinary skill in the art should appreciate, other molecular weight distributions may be possible and are within the scope of the present disclosure. The ratio of lactic acid to glycolic acid in the PLGA segments of the polymer may not be critical provided that the polymer has the required thermo-sensitive properties. In some embodiments, the PLGA segment of the copolymer has a lactic acid to glycolic acid ratio of about 1:1 and in some other embodiments, the PLGA segment of the copolymer has a lactic acid to glycolic acid ratio of about 3:1.

In some embodiments, the alpha-adrenergic agent described herein is added to the polymer solution prior to injection, and then the polymer/solvent/agent mixture is injected into the eyelid. In some embodiments, the formulation is injected intradermally, subcutaneously, pre-septally, post-septally, into the post septal fat pad, or intramuscularly. In some cases, the alpha-adrenergic agent is soluble in the solvent, and a homogenous solution of polymer and alpha-adrenergic agent may be used for injection. In other cases, the alpha-adrenergic agent is not soluble in the solvent, and a suspension or dispersion of the agent will result. In some embodiments, the suspension or dispersion is injected into the eyelid. In certain embodiments, upon injection, the solvent will dissipate and the polymer will solidify and entrap or encase the alpha-adrenergic agent within a solid or semi-solid matrix. The release of agent from these solid or semi-solid in-situ forming implants may follow the same general rules for release of a agent from a monolithic polymeric device. The release of drug may be affected by the size and shape of the implant, the loading of drug within the implant, the permeability factors involving the drug and the particular polymer, and the degradation of the polymer.

The amount of alpha-adrenergic agent incorporated into the injectable, in-situ, solid forming implant depends upon the desired release profile, the concentration of drug required for a biological effect, and the length of time that the drug has to be released for treatment. The lower limit of the alpha-adrenergic agent incorporated into the delivery system is dependent upon the activity of alpha-adrenergic agent and the length of time needed for treatment.

B. Thermosetting System

In certain embodiments, the liquid polymeric delivery system is a thermosetting system. In certain embodiment, the thermosetting system comprises one or more biocompatible polymers. In some embodiments, the thermosetting system comprises crosslinkable polymers which can be formed and cured in-situ through the use of a curing agent. The polymers may be first formed using a polyol initiator and catalyst to form polyol-terminated prepolymers which are further converted to acrylic ester-terminated prepolymers. Just prior to injection, a curing agent such as benzoyl peroxide or azobisisobutyronitrile is added to the acrylic prepolymer solution. Once injected, the crosslinking reaction proceeds until sufficient molecular weight has been obtained to cause the polymer to solidify. In some embodiments, the curing reaction is rapid and injection must take place almost immediately following the addition of the curing agent. These polymers may be formed primarily by the polymerization or copolymerization of biodegradable hydrophobic polylactides, polyglycolides, polycaprolactones and the like. In some embodiments, the biodegradable system comprises a bifunctional polyester synthesized from a bifunctional chain initiator such as ethylene glycol. In some embodiments, the biodegradable system comprises a trifunctional polyester synthesized from a trifunctional initiator such as trimethylolpropane. The amount of chain initiator may determine the resultant molecular weight of the polymer or copolymer. In certain embodiments, the gel matrix once formed will release the agent in a controlled manner and degrade to products which are easily metabolized and excreted.

In some embodiments, the solid implant formed within the injectable polymer solution will slowly biodegrade within the body and allow natural tissue to grow and replace the implant as it disappears. In some embodiments, the solid implant formed from the injectable system will release the alpha-adrenergic agent contained within its matrix at a controlled rate until the drug is depleted. In some embodiments, the polymer will degrade after the drug has been completely released. In some other embodiments, the drug will be completely released only after the polymer has degraded to a point where the non-diffusing drug has been exposed to the body fluids.

In various embodiments, the choice of polymer dictates the rate of release of the alpha-adrenergic agent.

Microneedles

In some embodiments, the alpha-adrenergic agent is packaged in or on microneedles. Microneedles are structures of typically micrometer to millimeter size, and designed to pierce the skin and deliver a composition to the epidermis or dermis of a subject. In some embodiments, the skin pierced by the microneedles is or is around the eyelid. Microneedles offer some advantages over traditional sub-cutaneous or intramuscular injections. First, the amount of alpha-adrenergic agent needed for administration can be smaller, cutting down on production cost and time. Second, the microneedle can be self-administered. Third, the alpha-adrenergic agent can be dried onto the microneedle, which greatly increases the stability of the composition at room temperatures. Moreover, microneedle administration is typically painless which may make it a more tolerated form of administration.

Microneedles are typically solid or hollow structures. When used as a solid support, the alpha-adrenergic agent for delivery can coat the microneedle (typically as a dried form) or can be released through hollow structures (e.g. liquid composition is injected or infused into the skin). Compositions can be on microneedles (for example, coated onto a surface of the microneedles after formation), or in microneedles (for example, forming part of the microneedle itself, such as by deposition into the interior of the microneedle, or by inclusion in a mixture used to form the microneedles). In some embodiments, the alpha-adrenergic agent is dissolved in the skin compartment or is injected into the skin. Microneedles are often formed in arrays, comprising multiple needle-like structures, such as on a patch. In some embodiments, the microneedle array is then applied directly to the skin for intradermal administration of a composition.

In some embodiments, the microneedle array patch is designed to be any shape or size. For example, a microneedle array patch for delivery of the alpha-adrenergic agent for cosmetic purposes can be shaped to mimic facial features, e.g., eyelids. In some embodiments, the microneedle array patch is of any size, but will preferably be the smallest size allowable to deliver a selected amount of the alpha-adrenergic agent.

The size and shape of the microneedles may also vary as desired. In some embodiments, the microneedles include a cylindrical portion upon which is positioned a conical portion having a tip. In some other embodiments, the microneedles have an overall pyramidal shape, or an overall conical shape. In general, the microneedle typically includes a base and a tip. In some embodiments, the tip has a radius that is less than or equal to about 1 micrometer. The microneedles are typically of a length sufficient to penetrate the stratum corneum and pass into the epidermis or dermis. In certain embodiments, the microneedles have a length (from their tip to their base) from about 0.1 micrometer to about 5 millimeters in length, for instance about 5 millimeters or less, 4 millimeters or less, from about 1 millimeter to about 4 millimeters, from about 500 micrometers to about 1 millimeter, from about 10 micrometers to about 500 micrometers, from about 30 micrometers to about 200 micrometers, or from about 250 micrometers to about 1500 micrometers.

In some embodiments, the size of individual microneedles is optimized depending upon the desired targeting depth, the strength requirements of the needle to avoid breakage in a particular tissue type, etc. In some embodiments, the cross-sectional dimension of a transdermal microneedle is from about 10 nm to about 1 mm, or from about 1 micrometers to about 200 micrometers, or from about 10 micrometers to about 100 micrometers. The outer diameter may be from about 10 micrometers to about 100 micrometers and the inner diameter of a hollow needle may be from about 3 micrometers to about 80 micrometers.

In some embodiments, the microneedles are arranged on a substrate in a variety of patterns, and such patterns are designed for a particular use. In some embodiments, the microneedles are spaced apart in a uniform manner, such as in a rectangular or square grid or in concentric circles. The spacing may depend on numerous factors, including height and width of the microneedles, the characteristics of a film to be applied to the surface of the microneedles, as well as the amount and type of a substance that is intended to be moved through the microneedles. An example arrangement of microneedles is a "tip-to-tip" spacing between microneedles of about 50 micrometers or more, in some embodiments about 100 to about 800 micrometers, and in some embodiments, from about 200 to about 600 micrometers.

In some embodiments, the microneedle composition is of any suitable material. Example materials include metals, ceramics, semiconductors, organics, polymers, and composites. In some embodiments, materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene and polyesters. In some embodiments, the microneedle is dissolvable, biosoluble, or biodegradable, or a combination thereof. A variety of dissolvable and/or biosoluble microneedles may be used. (see e.g., US20140200509, and WO2009021048 which are herein incorporated by reference in their entireties). Briefly, dissolvable microneedles may be composed of water soluble materials. These materials can include, by way of example, chitosan, collagen, gelatin, maltose, dextrose, galactose, alginate, agarose, cellulose such as carboxymethylcellulose or hydroxypropylcellulose, starch, and hyaluronic acid. In general, a selected material will be resilient enough to allow for penetration of the skin. Preferably, the dissolvable microneedle will dissolve in the skin within seconds, such as within about 5, 10, 15, 20, 25, 30, 45, 50, 60, 120, 180, or more seconds; or within minutes, such as within about 1, 2, 3, 4, 5, 6, 7, 8, 9, 10, 15, 20, 30, 60, 120 or more minutes. The dissolvable microneedle can encompass the entire microneedle, such that the entire microneedle structure will dissolve in the skin, or a dissolvable coating can be formed on a non-dissolvable support structure such that only the coating will dissolve in the skin. The microneedle may be coated with a polymer that is dissolvable, biodegradable, biosoluble, or a combination thereof.

In some embodiments, the alpha-adrenergic agent compositions are coated on the dissolvable microneedle or are contained within the dissolvable microneedle itself (e.g. by forming part of the dissolvable polymer matrix). In some embodiments, the alpha-adrenergic agent composition is directly coated onto microneedle structures, or is mixed with a polymer matrix prior to molding and polymerization of microneedle structures.

For examples of biodegradable microneedles, see e.g., WO200801068 and U.S. Pat. No. 6,334,856, each of which are hereby incorporated by reference.

A variety of suitable methods for making microneedles are available (see e.g. U.S. Pat. Nos. 6,312,612, 6,334,856, 7,182,747, 7,226,439, and WO2013137831). In some embodiments, the microneedles are manufactured using a variety of methods including, but not limited to, molding (e.g., self-molding, micromolding, microembossing, microinjection and the like), casting (e.g., die-casting), etching (e.g. soft microlithography techniques), and the like. The method of manufacture used will typically depend on the materials employed.

In some embodiments, the microneedle composition comprises one or more alpha-adrenergic agents.

In various embodiments, the release of the alpha-adrenergic agent is sustained over a prescribed amount of time. In various embodiments, the release of the alpha-adrenergic agent is sustained over a period of 4 hours or more. In various embodiments, the release of the alpha-adrenergic agent is sustained over a period of 8 hours or more. In various embodiments, the release of the alpha-adrenergic agent is sustained over a period of 12 hours or more. In various embodiments, the release of the alpha-adrenergic agent is sustained for up to one day, up to two days, up to three days, up to four days, up to five days, up to six days, up to seven days, up to one week, up to two weeks, up to three weeks, up to four weeks, up to one month, or up to two months.

In various embodiments, the microneedle array comprises from about 0.1 mg to about 10 mg of the alpha-adrenergic agent. In some embodiments, the microneedle array comprises about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, 2.1 mg, about 2.2 mg, about 2.3 mg, about 2.4 mg, about 2.5 mg, about 2.6 mg, about 2.7 mg, about 2.8 mg, about 2.9 mg, about 3.0 mg, 3.1 mg, about 3.2 mg, about 3.3 mg, about 3.4 mg, about 3.5 mg, about 3.6 mg, about 3.7 mg, about 3.8 mg, about 3.9 mg, about 4.0 mg, 4.1 mg, about 4.2 mg, about 4.3 mg, about 4.4 mg, about 4.5 mg, about 4.6 mg, about 4.7 mg, about 4.8 mg, about 4.9 mg, about 5.0 mg, 5.1 mg, about 5.2 mg, about 5.3 mg, about 5.4 mg, about 5.5 mg, about 5.6 mg, about 5.7 mg, about 5.8 mg, about 5.9 mg, about 6.0 mg, 6.1 mg, about 6.2 mg, about 6.3 mg, about 6.4 mg, about 6.5 mg, about 6.6 mg, about 6.7 mg, about 6.8 mg, about 6.9 mg, about 7.0 mg, 7.1 mg, about 7.2 mg, about 7.3 mg, about 7.4 mg, about 7.5 mg, about 7.6 mg, about 7.7 mg, about 7.8 mg, about 7.9 mg, about 8.0 mg, 8.1 mg, about 8.2 mg, about 8.3 mg, about 8.4 mg, about 8.5 mg, about 8.6 mg, about 8.7 mg, about 8.8 mg, about 8.9 mg, about 9.0 mg, 9.1 mg, about 9.2 mg, about 9.3 mg, about 9.4 mg, about 9.5 mg, about 9.6 mg, about 9.7 mg, about 9.8 mg, about 9.9 mg, about 10 mg of the alpha-adrenergic agent. In certain embodiments, any two of the doses in this paragraph may be combined to form a range of dosages included within the disclosure, e.g., the microneedle array comprises from about 1.0 mg to about 8.0 mg of an alpha-adrenergic agent.

In some embodiments, the microneedle array comprises from about 0.1 mg to about 10 mg of the alpha-adrenergic agent. In some embodiments, the microneedle array comprises from about 0.5 mg to about 8 mg of the alpha-adrenergic agent. In some embodiments, the microneedle array comprises from about 2 mg to about 5 mg of the alpha-adrenergic agent. In some embodiments, the microneedle array comprises from about 3 mg to about 5 mg of the alpha-adrenergic agent.

In some embodiments, the microneedle array comprises about 10 mg or less of the alpha-adrenergic agent. In some embodiments, the microneedle array comprises about 8 mg or less of the alpha-adrenergic agent. In some embodiments, the microneedle array comprises about 6 mg or less of the alpha-adrenergic agent. In some embodiments, the microneedle array comprises about 4 mg or less of the alpha-adrenergic agent.

In some embodiments, the microneedle array comprises at least about 1 mg of the alpha-adrenergic agent. In some embodiments, the microneedle array comprises at least about 2 mg of the alpha-adrenergic agent. In some embodiments, the microneedle array comprises at least about 3 mg of the alpha-adrenergic agent. In some embodiments, the microneedle array comprises at least about 4 mg of the alpha-adrenergic agent.

Methods of Use

In certain aspects, any of the compositions described herein may be used in the treatment of ptosis, for cosmetic alteration of the eyelid, or other related uses. The compositions of the disclosure are preferably applied topically on the eye or eyelid, are injected into the eyelid, or are released from implants in the eyelid or inserts near the eyelid. In certain embodiments, a controlled-release composition of the disclosure is used for the treatment of ptosis or cosmetic alteration of the eyelid or other related uses. The compositions used in the methods described herein may be selected from any of parenteral compositions, topical compositions, controlled-release compositions, microneedles, transdermal formulations and any other compositions described herein. In certain embodiment, the alpha-adrenergic agent of the methods described herein is an alpha-adrenergic agonist such as oxymetazoline or a salt thereof.

As used herein, the terms "treatment" or "treating" are used interchangeably herein. These terms refer to an approach for obtaining beneficial or desired results including but not limited to a therapeutic benefit, cosmetic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made. A cosmetic benefit may mean affecting a physical change to a subject that is desired by the subject.

As used herein, the term "effective amount" or "therapeutically effective amount" refers to the amount of a compound that is sufficient to affect the intended application, including but not limited to cosmetic treatment and disease treatment, as defined below. The therapeutically effective amount may vary depending upon the intended treatment application (in vivo), or the subject and disease condition being treated, e.g., the severity of the disease condition, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

In certain aspects, the disclosure provides a method for treating ptosis in a subject, comprising administering an effective amount of an alpha-adrenergic agent into the eyelid of the subject, such as administration through injection into the eyelid. In certain embodiments, the injection is administered intradermally, subcutaneously, pre-septally, post-septally, into the post-septal fat pad, or intramuscularly. In particular embodiments, the injection is administered intramuscularly into Müller's muscle or the levator muscle or both. In certain embodiments, the injection is administered subcutaneously, adjacent to Müller's muscle or the levator muscle.

In certain embodiments, the method for treating ptosis in a subject comprises administering a controlled-release composition into the eyelid of the subject. The controlled-release composition may be administered into the eyelid through surgical implantation or the controlled-release composition may be administered into the eyelid through injection. In certain embodiments, a controlled-release implant is injected into the eyelid of a subject. For example, a solid polymer-based implant may be injected into the eyelid of the subject.

In certain embodiments, a controlled-release implant is formed upon injection of an injectable polymeric composition, e.g., a thermosetting or thermoplastic composition. In certain such embodiments, the injectable polymeric composition forms a solid or semi-solid implant once injected into the tissue of the subject.

In certain embodiments, the disclosure provides a method of treating ptosis in a subject, comprising contacting one or more muscles in the eyelid with an effective amount of an alpha-adrenergic agent. In certain embodiments, the method of treating ptosis in a subject comprises contacting any one or more of the superior tarsal muscle, the orbitalis muscle, and the levator palpebrae superioris muscle. In certain embodiments, the method comprises directly contacting a muscle in the eyelid by, for example, injecting an alpha-adrenergic composition into the eyelid or implanting an alpha-adrenergic containing implant into the eyelid. The method may comprise indirectly contacting a muscle in the eyelid by, for example, applying a topical composition that permeates the skin of the eyelid. In certain such embodiments, the topical composition may be a transdermal formulation.

In certain embodiments, the method of the disclosure comprises contacting Müller's muscle and/or the levator muscles of the subject with an effective amount of an alpha-adrenergic agent. Müller's muscle, also referred to as the orbitalis muscle, is a smooth muscle that crosses from the infraorbital groove and sphenomaxillary fissure and is intimately united with the periosteum of the orbit. Müller's muscle lies at the back of the orbit and spans the infraorbital fissure.

In certain embodiments, contacting a muscle, such as Müller's muscle, of the subject occurs through parenteral administration of the alpha-adrenergic agent, such as through injection of the alpha-adrenergic agent into the eyelid of the subject. In certain embodiments, parenteral administration is injection of the alpha-adrenergic agent in an area on the face adjacent to the eyelid, such as injection into the angular vein.

In certain embodiments, the alpha-adrenergic agent is administered in a controlled-release composition. In certain embodiments, contacting a muscle, such as Müller's muscle, of the subject occurs through release of an alpha-adrenergic agent from a controlled-release composition, e.g., such as a polymer-based implant described herein, implanted into the eyelid of the subject. In certain embodiments, contacting a muscle, such as Müller's muscle, of the subject occurs through release of an alpha-adrenergic agent from an insert positioned under the eyelid or in contact with the eyelid of the subject.

In certain aspects, the disclosure provides a method for treating ptosis in a subject, comprising administering a controlled-release composition into the eyelid, in contact with the eyelid, or in close proximity to the eyelid of the subject, wherein the controlled-release composition releases a therapeutically effective amount of an alpha-adrenergic agent to the subject. In certain embodiments, the controlled-release composition is selected from any of the controlled-release composition described herein. In particular embodiments, the method comprises administering a controlled-release composition as an implant in the eyelid of the subject. In particular embodiments, the implant is biodegradable in vivo. In particular embodiments, the method comprises administering a controlled-release composition of an effective amount of an alpha-adrenergic agent to the subject as an injectable polymeric implant. In particular embodiments, the alpha-adrenergic agent of the method is oxymetazoline of a salt thereof.

In certain aspects, the disclosure provides a method for cosmetic treatment of a subject, comprising administering an effective amount of an alpha-adrenergic agent into the eyelid of the subject, such as administration through injection into the eyelid. In certain embodiments, the injection is administered intradermally, subcutaneously, pre-septally, post-septally, into the post-septal fat pad, or intramuscularly. In particular embodiments, the injection is administered intramuscularly into Müller's muscle or the levator muscle or both. In certain embodiments, the injection is administered subcutaneously, adjacent to Müller's muscle or the levator muscle.

In certain embodiments, the method for cosmetic treatment of a subject comprises administering a controlled-release composition into the eyelid of the subject. The controlled-release composition may be administered into the eyelid through surgical implantation or the controlled-release composition may be administered into the eyelid through injection. In certain embodiments, a controlled-release implant is injected into the eyelid of a subject. For example, a solid polymer-based implant may be injected into the eyelid of the subject.

In certain embodiments, a controlled-release implant of the cosmetic method is formed upon injection of an injectable polymeric composition, e.g., a thermosetting or thermoplastic composition. In certain such embodiments, the injectable polymeric composition forms a solid or semi-solid implant once injected into the tissue of the subject.

In certain embodiments, the disclosure provides a method of cosmetic therapy of a subject comprising contacting one or more muscles in the eyelid with an effective amount of an alpha-adrenergic agent. In certain embodiments, the method of cosmetic therapy of a subject comprises contacting any one or more of the superior tarsal muscle, the orbitalis muscle, and the levator palpebrae superioris muscle. In certain embodiments, the method comprises directly contacting a muscle in the eyelid by, for example, injecting an alpha-adrenergic composition into the eyelid or implanting an alpha-adrenergic containing implant into the eyelid. The method may comprise indirectly contacting a muscle in the eyelid by, for example, applying a topical composition that permeates the skin of the eyelid. In certain such embodiments, the topical composition may be a transdermal formulation.

In certain embodiments, the method of cosmetic therapy comprises contacting Müller's muscle and/or the levator muscles of the subject with an effective amount of an alpha-adrenergic agent. In certain embodiments, contacting a muscle, such as Müller's muscle, of the subject occurs through parenteral administration of the alpha-adrenergic agent, such as through injection of the alpha-adrenergic agent into the eyelid of the subject. In certain embodiments, parenteral administration is injection of the alpha-adrenergic agent in an area on the face adjacent to the eyelid, such as injection into the angular vein.

In certain embodiments, the method of cosmetic therapy of a subject comprises administering an alpha-adrenergic agent in a controlled-release composition. In certain embodiments, direct contacting a muscle such as Müller's muscle of the subject occurs through release of an alpha-adrenergic agent from a controlled-release composition, e.g., such as a polymer-based implant described herein, implanted into the eyelid of the subject. In certain embodiments, indirect contacting a muscle such as Müller's muscle of the subject occurs through release of an alpha-adrenergic agent from an insert positioned under the eyelid or in contact with the eyelid of the subject.

In certain aspects, the disclosure provides a method for cosmetic therapy of a subject, comprising administering a controlled-release composition into the eyelid, in contact with the eyelid, or in close proximity to the eyelid of the subject, wherein the controlled-release composition releases a therapeutically effective amount of an alpha-adrenergic agent to the subject. In certain embodiments, the controlled-release composition is selected from any of the controlled-release compositions described herein. In particular embodiments, the method of cosmetic therapy comprises administering a controlled-release composition as an implant in the eyelid of the subject. In particular embodiments, the implant is biodegradable in vivo. In particular embodiments, the method comprises administering a controlled-release composition of an effective amount of an alpha-adrenergic agent to the subject as an injectable polymeric implant. In particular embodiments, the alpha-adrenergic agent of the method is oxymetazoline of a salt thereof.

In certain embodiments, the controlled-release composition of the disclosure provides sustained-release of the alpha-adrenergic agent over a period of two weeks or more, such as three weeks or more, such as four weeks or more, such as five weeks of more, such as six weeks or more, such as seven weeks or more, such as eight weeks or more such as none weeks or more, such as ten weeks or more, such as eleven weeks or more, such as twelve weeks or more, such as thirteen weeks or more, such as fourteen weeks or more, such as fifteen weeks or more, or even such as sixteen weeks or more.

In certain embodiments, the controlled-release composition of the disclosure provides sustained-release of the alpha-adrenergic agent over a period of about two weeks, about three weeks, about four weeks, about five weeks, about six weeks, about seven weeks, about 8 weeks, about nine weeks, about ten weeks, about eleven weeks, about twelve weeks, about thirteen weeks, about fourteen weeks, about fifteen weeks, or even about sixteen weeks. In certain embodiments, the controlled-release composition of the disclosure provides sustained-release of the alpha-adrenergic agent over a period of about one month, about two months, about three months, about four months, about five months, about six months, about seven months, about eight months, about nine months, about ten months, about eleven months, or even about twelve months. In certain embodiments, any two of the time frames in this paragraph may be combined to form a range of time frames included within the disclosure, e.g., the controlled-release composition of the disclosure provides sustained-release of the alpha-adrenergic agent over a period of about three weeks to about four months.

The term "controlled release", as used herein, refers to release of predetermined amounts of an alpha-adrenergic agent into the body over a specified time period. Controlled-release compositions include sustained-release compositions, delayed-release compositions, targeted-release drug products, etc. The term "sustained-release", as used herein, refers to release of an alpha-adrenergic agent at a predetermined rate in order to maintain a constant or near-constant drug concentration for a period of time.

In certain aspects, the disclosure provides a method for increasing the vertical separation of the upper and lower eyelids of a subject relative to a pre-treatment separation, comprising administering an effective amount of an alpha-adrenergic agent to the eye or eyelid of a subject. In particular embodiments, the subject does not have ptosis. In certain embodiments, the alpha-adrenergic agent is administered as a controlled-release composition. In certain embodiments, the alpha-adrenergic is administered topically to the eye or eyelid. In particular embodiments, the alpha-adrenergic agent is administered to the eyelid of the subject, such as into the eyelid of a subject. In certain embodiments, the vertical separation of the upper and lower eyelids is increased by 10 percent or more relative to the pre-treatment separation.

In certain embodiments, the methods of the disclosure increase the vertical separation of the upper and lower eyelid by about 1% or more, about 2% or more, about 3% or more, about 4% or more, about 5% or more about 6% or more, about 7% or more, about 8% or more, about 9% or more, about 10% or more, about 11% or more, about 12% or more, about 13% or more, about 14% or more, about 15% or more, about 16% or more, about 17% or more about 18% or more, about 19% or more, about 20% or more, about 21% or more, about 22% or more, about 23% or more, about 24% or more, about 25% or more, about 26% or more, about 27% or more, about 28% or more about 29% or more, about 30% or more, about 31% or more, about 32% or more, about 33% or more, about 34% or more, about 35% or more, about 36% or more, about 37% or more, about 38% or more about 39% or more, about 40% or more, about 41% or more, about 42% or more, about 43% or more, about 44% or more, about 45% or more, about 46% or more, about 47% or more, about 48% or more about 49% or more, about 50% or more, relative to the pre-treatment vertical separation of the upper and lower eyelids.

In certain embodiments, the methods of the disclosure increase the distance of the upper eyelid from the midpupil. Drooping eyelids or ptotic eyelids may have a distance between the upper eyelid and the midpupil of about 2 mm or less. In certain embodiments, methods of the disclosure increase the distance between the upper eyelid and midpupil to about 2 mm or more, about 2.1 mm or more, about 2.2 mm or more, about 2.3 mm or more, about 2.4 mm or more, about 2.5 mm or more, about 2.6 mm or more, about 2.7 mm or more, about 2.8 mm or more, about 2.9 mm or more, about 3.0 mm or more, about 3.1 mm or more, about 3.2 mm or more, about 3.3 mm or more, about 3.4 mm or more, about 3.5 mm or more, about 3.6 mm or more, about 3.7 mm or more, about 3.8 mm or more, about 3.9 mm or more, or even about 4.0 mm or more, relative to the pre-treatment distance of the upper eyelid from the midpupil.

In certain embodiments, methods of the disclosure reduce the asymmetry between the two upper eyelids.

In certain embodiments, the disclosure provides a method of changing the location of the visual axis of a subject, comprising administering an effective amount of an alpha-adrenergic agent to the eye or into the eyelid of the subject. In particular embodiments, the subject does not have ptosis. In certain embodiments, the alpha-adrenergic agent is administered as a controlled-release composition. In certain embodiments, the alpha-adrenergic is administered topically to the eye or eyelid. In particular embodiments, the alpha-adrenergic agent is administered to the eyelid of the subject, such as into the eyelid of a subject. In certain embodiment, changing the location of the visual axis improves the subject's vision. Improving the subject's vision may include any of: improving visual acuity, improving contrast sensitivity, reducing glare and halos, and increasing the amount of aperture through which the subject has good vision.

Diagnostic Methods

In certain embodiments, the disclosure provides methods for screening subjects who would benefit from the methods disclosed herein, using an alpha-adrenergic agent. In particular embodiments, an alpha-adrenergic agent is administered topically as a screening dose to the eye or eyelid of a subject to determine whether the eyelid of the subject responds to the administration of the alpha-adrenergic agent. In certain embodiments, if the subject's eyelid responds to the topical administration of the alpha-adrenergic agent, the subject may be administered a treatment regimen of an alpha-adrenergic agent in the form of a topical or parenteral administration. In particular embodiments, a subject is administered a topical alpha-adrenergic agent and if the eyelid responds to the administration, the subject is administered one or more doses of alpha-adrenergic agent by injection into the eyelid, as described in the methods disclosed herein.

In certain embodiments, the "eyelid responds to the administration" by retracting, such that the vertical separation of the lower and upper eyelids of the eye treated increases. For example, a subject is administered a topical alpha-adrenergic agent, e.g., oxymetazoline eye drops in the eye, and the upper eyelid of said eye retracts upwardly such that the vertical separation of the lower and upper eyelids increases by about 0.5 mm or more, such as about 1 mm or more or even about 2 mm or more.

If the upper eyelid of the eye treated with an alpha-adrenergic agent responds to the screening dose, any of the methods of use described in the preceding section may be used on the subject. For example, if the upper eyelid of the subject's eye treated with an alpha-adrenergic agent responds to the screening administration, the subject may receive an injection of an alpha-adrenergic agent, the subject may apply a topical composition of an alpha-adrenergic agent into the eye or on the eyelid or any combination thereof.

In certain embodiments, the screening method provides information regarding suitable dosages or methods of administration of alpha-adrenergic agents. For example, a subject's eyelid may not retract or retract minimally upon administration of a screening dosage of an alpha-adrenergic agent. As used herein, "retract minimally" may refer to an increase in vertical separation of the upper and lower eyelids of less than 2 mm such as from about 0.1 mm to about 2 mm, about 0.1 mm to about 1.5 mm, about 0.1 mm to about 1 mm, about 0.1 to about 0.8 mm or even about 0.1 to about 0.5 mm relative to the position of the eyelids prior to administration of the alpha-adrenergic agent. When a subject's eyelid does not retract or retracts minimally upon administration of the topical alpha-adrenergic agent screening dose, the subject may receive a second screening dose that is higher than the first screening dose to determine whether the subject's eyelid responds to the higher dose.

In certain embodiments, the response of the subject to the topical screening dose of the alpha-adrenergic agent may be used to determine the dose or frequency of administration of an alpha-adrenergic agent administered to the subject. For example, a subject's eyelid displays a large retractive response upon administration of the topical screening dose, and therefore the subject may be prescribed a low dose of an alpha-adrenergic agent. Alternatively, a subject's eyelid may display a small retractive response upon administration of the screening dose, and therefore the subject may be prescribed a high dose of alpha-adrenergic agent.

In certain embodiments, the administration method of an alpha-adrenergic agent may be prescribed based upon the subject's response to the screening dose. For example, a subject's eyelid displays a large retractive response upon administration of the topical screening dose, and therefore the subject may be prescribed a topical treatment regimen. Alternatively, a subject's eyelid may display a small retractive response upon administration of the screening dose, and therefore the subject may be prescribed a parenteral treatment regimen either alone or in combination with a topical treatment regimen.

All publications, patents, and patent applications mentioned in this specification are herein incorporated by reference to the same extent as if each individual publication, patent, or patent application was specifically and individually indicated to be incorporated by reference.

The invention is further described in detail by reference to the following examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Embodiments contemplated herein include embodiments P1 to P48.

Embodiment P1. A controlled-release composition, comprising an alpha-adrenergic agent and a delivery system which controls the release of the alpha-adrenergic agent.

Embodiment P2. The controlled-release composition of embodiment P1, wherein the composition is selected from a sustained-release composition, a prolonged release composition, a pulsatile release composition and a delayed-release composition.

Embodiment P3. The controlled-release composition of embodiment P1 or P2, wherein the delivery system is selected from polymer-based systems, porous matrices, hydrogel release systems, and peptide-based systems.

Embodiment P4. The controlled-release composition of any embodiments P1 to P3, wherein the composition is a sustained-release composition.

Embodiment P5. The controlled-release composition of embodiment P4, wherein the sustained-release composition is formulated for injection.

Embodiment P6. The controlled-release composition of embodiment P6, wherein the composition is formulated for injection intradermally, subcutaneously, pre-septally, post-septally, into the post-septal fat pad, or intramuscularly.

Embodiment P7. The controlled-release composition of any one of embodiments P1 to P6, wherein the composition comprises from 0.2 to 10 mg of the alpha-adrenergic agent.

Embodiment P8. The controlled-release composition of embodiment P7, wherein the composition comprises from 0.5 to 8 mg of the alpha-adrenergic agent.

Embodiment P9. The controlled-release composition of embodiment P7, wherein the composition comprises 0.5 to 3 mg of the alpha-adrenergic agent.

Embodiment P10. The controlled-release composition of embodiment P7, wherein the composition comprises 3 to 6 mg of the alpha-adrenergic agent.

Embodiment P11. The controlled-release composition of embodiment P4, wherein the sustained-release composition is formulated for topical administration.

Embodiment P12. The controlled-release composition of embodiment P1, wherein the composition is formulated for administration to the eyelid.

Embodiment P13. The controlled-release composition of embodiment P11 or P12, wherein the composition comprises 0.2 to 6 mg of an alpha-adrenergic agent per dose.

Embodiment P14. The controlled-release composition of embodiment P13, wherein the composition comprises 0.5 to 4 mg of an alpha-adrenergic agent per dose.

Embodiment P15. The controlled-release composition of embodiment P14, wherein the composition comprises from 0.5 to 3 mg of an alpha-adrenergic agent per dose.

Embodiment P16. The controlled-release composition of any one of embodiments P1 to P15, wherein the alpha-adrenergic agent is selected from naturally occurring or synthetic alpha-adrenergic agents.

Embodiment P17. The controlled-release composition of any one of embodiments P1 to P16, wherein the alpha-adrenergic agent is selected from an alpha-1 agonist and an alpha-2 agonist.

Embodiment P18. The controlled-release composition of any one of embodiments P1 to P17, wherein the alpha-adrenergic agent is selected from amidephrine, anisodamine, anisodine, chloroethylclonidine, cirazoline, desvenlafaxine, dipivefrine, dopamine, ephedrine, epinephrine (adrenaline), etilefrine, ethylnorepinephrine, 5-fluronorepinephrine, 6-fluoronorepinephrine, indanidine, levonordefrin, metaraminol, methoxamine, methyldopa, midodrine, naphazoline, norepinephrine (noradrenaline), octopamine, oxymetazoline, phenylephrine, phenylpropanolamine, pseudoephedrine, synephrine, tetrahydrozoline, xylometazoline, 6-(5-fluoro-2-pyrimidin-5-yl-phenyl)-6,7-dihydro-5H-pyrrolo[1,2-a]imidazole, A-61603 (N-[5-(4,5-dihydro-1H-imidazol-2-yl)-2-hydroxy-5,6,7,8-tetrahydronaphthalen-1-yl]methanesulfonamide) and salts of any one thereof.

Embodiment P19. The controlled-release composition of embodiment P18, wherein the alpha-adrenergic agent is oxymetazoline or a salt thereof.

Embodiment P20. A method for treating ptosis in a subject, comprising injecting a therapeutically effective amount of an alpha-adrenergic agent into the eyelid of the subject.

Embodiment P21. A method for cosmetic therapy of a subject, comprising injecting a therapeutically effective amount of an alpha-adrenergic agent into the eyelid of the subject.

Embodiment 22. The method of embodiment P20 or P21, wherein the injection is administered intradermally, subcutaneously, pre-septally, post-septally, into the post-septal fat pad, or intramuscularly.

Embodiment P23. The method of embodiment P22, wherein the alpha-adrenergic agent is administered intramuscularly.

Embodiment P24. The method of embodiment P23, wherein the intramuscular injection is administered into Müller's muscle or the levator muscle or both.

Embodiment P25. The method of embodiment P21, wherein the injection is administered adjacent to Müller's muscle or the levator muscle or both.

Embodiment P26. The method of any one of embodiments P20 to P25, wherein the alpha-adrenergic agent is formulated as the controlled-release composition of any one of embodiments P1 to P10.

Embodiment P27. The method of any of embodiment P20 to P26, wherein the alpha-adrenergic agent is oxymetazoline or a salt thereof Embodiment P28. A method for treating ptosis in a subject, comprising directly contacting Müller's muscle with an effective amount of an alpha-adrenergic agent.

Embodiment P29. A method for cosmetic therapy of a subject, comprising directly contacting Müller's muscle with an effective amount of an alpha-adrenergic agent.

Embodiment P30. The method of embodiment P28 or P29, wherein the direct contact occurs through release of an alpha-adrenergic agent from an implant in the eyelid of the subject.

Embodiment P31. The method of embodiment P28 or P29, wherein the direct contact occurs through injection of the alpha-adrenergic agent into Müller's muscle.

Embodiment P32. The method of any one of embodiments P28 to P31, wherein the alpha-adrenergic agent is formulated as the controlled-release composition of any one of embodiments P1 to P10.

Embodiment P33. The method of any one of embodiments P28 to P32, wherein the alpha-adrenergic agent is oxymetazoline or a salt thereof.

Embodiment P34. A method for treating ptosis in a subject, comprising administering a controlled-release composition of an alpha-adrenergic agent to the eyelid of the subject wherein the controlled-release composition releases an effective amount of an alpha-adrenergic agent to the subject over a period of time.

Embodiment P35. A method for cosmetic therapy of a subject, comprising administering a controlled-release composition of an alpha-adrenergic agent to the eyelid of the subject wherein the controlled-release composition releases an effective amount of an alpha-adrenergic agent to the subject over a period of time.

Embodiment P36. The method of embodiment P34 or P35, wherein the controlled-release composition is selected from any one of embodiments P1 to P19.

Embodiment P37. The method of embodiment P35, wherein the controlled-release composition is administered topically to the eyelid.

Embodiment P38. The method of embodiment P37, wherein the controlled-release composition releases an effective amount of an alpha-adrenergic agent to the subject over a period of 6 hours or more.

Embodiment P39. The method of embodiment P35, wherein the controlled-release composition is administered by injection into the eyelid.

Embodiment P40. The method of embodiment P39, wherein the controlled-release composition is administered as an injectable polymeric implant.

Embodiment P41. The method of embodiment P39 or P40, wherein the controlled-release composition releases an effective amount of an alpha-adrenergic agent to the subject over a period of 2 weeks or more.

Embodiment P42. A method for increasing the vertical separation of the upper and lower eyelids of a subject, comprising administering an effective amount of an alpha-adrenergic agent to the eye or eyelid of a subject.

Embodiment P43. The method of embodiment P42, wherein the subject does not have ptosis.

Embodiment P44. The method of embodiment P42 or P43, wherein the alpha-adrenergic agent is administered as a controlled-release composition selected from any one of embodiments P1 to P14.

Embodiment P45. The method of embodiment P42 or P43, wherein the alpha-adrenergic agent is administered topically to the eye or eyelid.

Embodiment P46. The method of embodiment P45, wherein the alpha-adrenergic agent is administered to the eyelid of the subject.

Embodiment P47. The method of embodiment P42 or P43, wherein the alpha-adrenergic agent is injected into the eyelid of the subject.

Embodiment P48. The method of any one of embodiments P42 to P47, wherein the vertical separation of the upper and lower eyelids is increased by 10 percent or more relative to the pre-treatment separation of the upper and lower eyelids.

EXAMPLES

Example 1

Evaluation of the Effect on the Eyelid Retraction After Administration of Oxymetazoline Solutions in Rabbits Rabbits without ocular pathology received oxymetazoline solutions by ocular injection. The evolution was tested postoperative, 1, 2, 3, 7, 10, and 14 day after oxymetazoline solutions administration. Eyelids were analyzed by histology at the end of the experiment. Endpoints included inflammation, fibrosis, pre- and post-septal fat, status of levator muscle and Müller's muscle, presence of vascular injury or necrosis or ischemic injury to eyelid tissues.

Material
    Animals: female New Zealand rabbits (2.5-3 kg)
    Sedation: atropine sulfate and midazolam IV (ear vein)
    Anesthesia: induction with Propofol 1% (10 mg/kg) by ear vein
    Maintenance with isoflurane (inhalant anesthesia)
    Oxymetazoline solutions
    Slit lamp
Method
Baseline measures (1st phase)
I. Animals (n=2); 2.5-3 kg New Zealand rabbit
II. Without sedation and anesthesia
III. Photographic record with a ruler (to serve as a standard measure of distance). Three sets of photos per measurements taken in dim lighting to keep rabbits from squinting
IV. 50 µl of 10% phenylephrine was administered via topical into the right eye (RE)
V. Photographic record with a ruler. Three sets of photos per measurements. After 20-30 minutes post-dose.
VI. Animals returned to animal housing.
Test Article (oxymetazoline solutions) (2nd phase)
I. Animals (n=3/each group); 2.5-3 kg New Zealand rabbit
II. Photographic record with a ruler (to serve as a standard measure of distance). Three sets of photos per measurements taken in dim lighting to keep rabbits from squinting.
III. Sedation with atropine sulfate and midazolam
IV. Induction with Propofol
V. Maintenance with isoflurane
VI. Ocular injection of oxymetazoline solutions or PBS (phosphate-buffered saline)
    a. Group A: oxymetazoline 1 mg/ml in PBS (RE) and PBS (LE)
    b. Group B: oxymetazoline 3 mg/ml in PBS (RE) and PBS (LE)
    c. Group C: oxymetazoline 10 mg/ml in PBS (RE) and PBS (LE)
All animals were administered 100 µl (0.1 ml) of the oxymetazoline solution (RE) or PBS vehicle control (LE) via an injection into the post-septal fat pad, adjacent to Müller's muscle of both eyelids on Day 0. For this injection, a 30G needle was used; test article was administered at least 4 mm away from the site of the needle entry to prevent reflux of fluid through the hole.
VII. Follow-up.
VIII. Euthanized animals 14 days after the injection of oxymetazoline solutions to process the eyelids tissues.
    a. Harvest both eyelids from each animal and store in formalin
    b. Histology (H/E staining)

Follow-Up

Follow-Up Included:
- Eyelid retraction/ptosis measurements & digital photos with eyes directly facing camera and a ruler in the frame of the photograph to standardize distances. Three sets of photos per measurement taken in dim lighting to keep rabbits from squinting.
- Slit-lamp biomicroscopy
- Daily general health observations
- Body weights prior to dosing and prior to sacrifice Study Variables I. Palpebral Fissure Distance
II. Margin reflex distance 1

Results

Group A (1 mg/ml)

Notes:
pre-injection. Oxy injection performed without incidents;
Day 2: pressure applied to close eyelid in Right Eye (3 h post-injection). Annimal show ocular discomfort
Day 3 morning: pressure applied to close eyelid in Right Eye

|  |  | #1 (Male. 2.8 Kg)/ #2 (Male 3 Kg)/#3 (Male, 3 Kg) | |
|---|---|---|---|
|  |  | Right Eye (RE) | Left Eye (LE) |
| Day 2 | Conjuctival Congestion | +/+/+ | +/+/+ |
|  | Chemosis | +/+/+ | +/+/+ |
|  | Redness | +/+/+ | +/+/+ |
|  | Threat Test | Abolished/Abolished/Abolished | Delayed/+/Delayed |
|  | Palpebral Reflex | Abolished/Abolished/Abolished | +/+/+ |
| Day 3 morning | Conjuctival Congestion | +/+/+ | −/−/− |
|  | Chemosis | +/+/+ | −/−/− |
|  | Redness | +/+/+ | +/+/+ |
|  | Threat Test | Abolished/Abolished/Abolished | +/+/+ |
|  | Palpebral Reflex | Delayed/Delayed/Delayed | +/+/+ |
| Day 3 afternoon | Conjuctival Congestion | +/+/+ | −/−/− |
|  | Chemosis | −/−/− | −/−/− |
|  | Redness | −/−/− | −/−/− |
|  | Threat Test | Delayed/Delayed/Delayed | +/+/+ |
|  | Palpebral Reflex | +/+/+ | +/+/+ |
| Day 4 morning | Conjuctival Congestion | +/+/+ | −/−/− |
|  | Chemosis | −/−/− | −/−/− |
|  | Redness | −/−/− | −/−/− |
|  | Threat Test | Delayed/Delayed/Delayed | +/+/+ |
|  | Palpebral Reflex | +/+/+ | +/+/+ |
| Day 4 afternoon | Conjuctival Congestion | +/+/+ | −/−/− |
|  | Chemosis | −/−/− | −/−/− |
|  | Redness | −/−/− | −/−/− |
|  | Threat Test | Delayed/Delayed/Delayed | +/+/+ |
|  | Palpebral Reflex | +/+/+ | +/+/+ |
| Day 5 | Conjuctival Congestion | −/−/− | −/−/− |
|  | Chemosis | −/−/− | −/−/− |
|  | Redness | −/−/− | −/−/− |
|  | Threat Test | +/+/+ | +/+/+ |
|  | Palpebral Reflex | +/+/+ | +/+/+ |
| Day 6 | Conjuctival Congestion | −/−/− | −/−/− |
|  | Chemosis | −/−/− | −/−/− |
| Day 7 | Redness | −/−/− | −/−/− |
|  | Threat Test | +/+/+ | +/+/+ |
|  | Palpebral Reflex | +/+/+ | +/+/+ |
|  | Conjuctival Congestion | −/−/− | −/−/− |
|  | Chemosis | −/−/− | −/−/− |
|  | Redness | −/−/− | −/−/− |
|  | Threat Test | +/+/+ | +/+/+ |
|  | Palpebral Reflex | +/+/+ | +/+/+ |
| Day 8 | Conjuctival Congestion | −/−/− | −/−/− |
|  | Chemosis | −/−/− | −/−/− |
|  | Redness | −/−/− | −/−/− |
|  | Threat Test | +/+/+ | +/+/+ |
|  | Palpebral Reflex | +/+/+ | +/+/+ |

Group B (3 mg/ml)

Notes:
pre-injection. Oxy injection performed without incidents;
Day 2: pressure applied to close eyelid in Right Eye (3 h post-injection). Annimal show ocular discomfort
Day 3 morning: pressure applied to close eyelid in Right Eye
Day 3 afternoon: pressure applied to close eyelid in Right Eye
Day 4 morning: pressure applied to close eyelid in Right Eye

|  |  | #1 (Male. 3 Kg)/#2 (Male 2.9 Kg) | |
|---|---|---|---|
|  |  | Right Eye (RE) | Left Eye (LE) |
| Day 2 | Conjuctival Congestion | +/+ | +/+ |
|  | Chemosis | +/+ | +/+ |
|  | Redness | +/+ | +/+ |
|  | Threat Test | Abolished/Abolished | Delayed/+/Delayed |
|  | Palpebral Reflex | Abolished/Abolished | +/+ |
| Day 3 morning | Conjuctival Congestion | +/+ | −/− |
|  | Chemosis | +/+ | −/− |
|  | Redness | +/+ | +/+ |
|  | Threat Test | Abolished/Abolished | +/+ |
|  | Palpebral Reflex | Delayed/Delayed | +/+ |
| Day 3 afternoon | Conjuctival Congestion | +/+ | −/− |
|  | Chemosis | −/+ | −/− |
|  | Redness | −/− | −/− |
|  | Threat Test | Abolished/Abolished | +/+ |
|  | Palpebral Reflex | Delayed/Delayed | +/+ |
| Day 4 morning | Conjuctival Congestion | +/+ | −/− |
|  | Chemosis | −/− | −/− |
|  | Redness | −/− | −/− |
|  | Threat Test | Delayed/Delayed | +/+ |
|  | Palpebral Reflex | Delayed/Delayed | +/+ |
| Day 4 afternoon | Conjuctival Congestion | +/+ | −/− |
|  | Chemosis | −/− | −/− |
|  | Redness | −/− | −/− |
|  | Threat Test | Delayed/Delayed | +/+ |
|  | Palpebral Reflex | +/+ | +/+ |
| Day 5 | Conjuctival Congestion | −/− | −/− |

-continued

| | | #1 (Male. 3 Kg)/#2 (Male 2.9 Kg) | |
| --- | --- | --- | --- |
| | | Right Eye (RE) | Left Eye (LE) |
| | Chemosis | −/− | −/− |
| | Redness | −/− | −/− |
| | Threat Test | Delayed/ | +/+ |
| | Palpebral Reflex | +/+ | +/+ |
| Day 6 | Conjuctival Congestion | −/− | −/− |
| | Chemosis | −/− | −/− |
| | Redness | −/− | −/− |
| | Threat Test | +/+ | +/+ |
| | Palpebral Reflex | +/+ | +/+ |
| Day 7 | Conjuctival Congestion | −/− | −/− |
| | Chemosis | −/− | −/− |
| | Redness | −/− | −/− |
| | Threat Test | +/+ | +/+ |
| | Palpebral Reflex | +/+ | +/+ |
| Day 8 | Conjuctival Congestion | −/− | −/− |
| | Chemosis | −/− | −/− |
| | Redness | −/− | −/− |
| | Threat Test | +/+ | +/+ |
| | Palpebral Reflex | +/+ | +/+ |

Example 2

Diagnostic Method

A single drop of phenylephrine 2.5% or 10% is administered to the eye of a subject with ptosis or a subject who would like to elevate the upper eyelid for cosmetic purposes or otherwise. The treated eye is observed to see how the eyelid responds to the administration. The response of the eyelid to the phenylephrine can be used to determine whether the patient will be responsive to treatment with an alpha-adrenergic agent for treating ptosis or elevating the upper eyelid for cosmetic or other purposes. The dosage, frequency and methods of administration of the alpha-adrenergic agent for treating ptosis or elevating the upper eyelid for cosmetic or other purposes can also be determined.

Example 3

Treatment of Ptosis

A sustained-release composition of oxymetazoline, e.g., from about 0.5 mg to about 4 mg, is injected into one eyelid, for unilateral ptosis, or both eyelids, for bilateral ptosis, of a subject suffering from ptosis. The subject receives the injection as part of a treatment regimen that includes biweekly, monthly or bimonthly injections of oxymetazoline. The subject may also apply a topical pharmaceutical composition of oxymetazoline, e.g., 0.5 mg to 2 mg per dose, on an as needed basis.

Example 4

Cosmetic Treatment by Injection

A sustained-release composition of oxymetazoline, e.g., from about 0.5 mg to about 4 mg, is injected into the eyelid of a subject for cosmetic purposes. The subject receives the injection as part of a treatment regimen that includes biweekly, monthly or bimonthly injections of oxymetazoline. The subject may also apply a topical pharmaceutical composition of oxymetazoline on an as needed basis.

Example 4

Cosmetic Treatment by Topical Application to the Exterior Surface of the Eyelid

A dermatological composition of oxymetazoline, formulated for administration to the exterior surface of the upper eyelid, is applied to the eyelid of a subject in need thereof. The composition may be formulated as a lotion, a cream or make-up such as eyeshadow or eyeliner. The subject applies the composition as needed, such as once or twice daily.

We claim:

1. A method for increasing the vertical separation of the upper and lower eyelids of an eye of a subject, comprising
   administering to the exterior surface of the upper eyelid of the subject a gel composition comprising an effective amount of oxymetazoline or a salt thereof and a permeation enhancer,
   wherein the effective amount of oxymetazoline or a salt thereof is from about 0.5 mg to 8 mg per dose, and
   wherein the increasing the vertical separation of the upper and lower eyelids comprises retraction of the upper eyelids by about 0.5 mm or more.

2. The method of claim 1, wherein the increasing the vertical separation of the upper and lower eyelids comprises retracting the upper eyelid by about 1 mm or more.

3. The method of claim 1, wherein the gel composition comprises from about 3 to 6 mg of oxymetazoline or a salt thereof per dose.

4. The method of claim 1, wherein the permeation enhancer is less than 40% by weight of the gel composition.

5. The method of claim 1, wherein the permeation enhancer is less than 20% by weight of the gel composition.

6. The method of claim 1, wherein the permeation enhancer is selected from ethanol, propylene glycol, dodecyl-N,N-dimethyl-aminoacetate, ethylacetate, azone, sodium dodecyl sulfate, d-limonene, oleic acid, 1,3-diphenyl-urea, N-methyl-2-pyrrolidone, beta-cyclodextrin, and dimethylsulfoxide.

7. The method of claim 1, wherein the permeation enhancer comprises an alcohol.

8. The method of claim 7, wherein the permeation enhancer comprises propylene glycol.

9. The method of claim 1, wherein the permeation enhancer increases skin permeation of oxymetazoline or a salt thereof by about 2-fold or greater relative to a composition without the permeation enhancer.

10. The method of claim 9, wherein the permeation enhancer increases skin permeation of oxymetazoline or a salt thereof by about 3-fold or greater relative to a composition without the permeation enhancer.

11. The method of claim 1, wherein the permeation enhancer increases skin permeation of oxymetazoline or a salt thereof by about 0.5 mm or more relative to a composition without the permeation enhancer.

12. The method of claim 1, wherein oxymetazoline or a salt thereof permeates through the stratum corneum and septal fat pad to contact Müller's muscle.

13. The method of claim 1, wherein the administering comprises administering the gel composition at most 3 times per day.

14. The method of claim 1, wherein the gel composition is a controlled-release composition.

15. The method of claim 1, wherein the gel composition further comprises one or more dermatologically acceptable carriers.

16. The method of claim 1, wherein the one or more dermatologically acceptable carriers are individually selected from buffers, preservatives, gelling agents, rheological modifiers and stabilizers, moisturizers, and humectants.

17. The method of claim 1, further comprising one or more cosmetic excipients.

18. The method of claim 17, wherein the one or more cosmetic excipients are individually selected from sunscreens, fragrances, pigments and antioxidants.

19. The method of claim 1, wherein retraction of the upper eyelids by about 0.5 mm or more comprises an increase in the vertical separation of the upper and lower eyelids relative to the position of the eyelids prior to administration of oxymetazoline or a salt.

* * * * *